US012667569B2

(12) United States Patent
Mezzaroma et al.

(10) Patent No.: US 12,667,569 B2
(45) Date of Patent: Jun. 30, 2026

(54) USE OF SEPIAPTERIN AND METABOLITES THEREOF TO TREAT RADIATION EXPOSURE

(71) Applicants: PTC Therapeutics MP, Inc., South Plainfield, NJ (US); Virginia Commonwealth University, Richmond, VA (US)

(72) Inventors: Eleonora Mezzaroma, Glen Allen, VA (US); Christopher Rabender, Chesterfield, VA (US); Ross Mikkelsen, Richmond, VA (US); Vasily Yakovlev, Richmond, VA (US); Neil Smith, Cary, NC (US)

(73) Assignees: PTC Therapeutics MP, Inc., Warren, NJ (US); Virginia Commonwealth University, Richmond, VA (US)

( * ) Notice: Subject to any disclaimer, the term of this patent is extended or adjusted under 35 U.S.C. 154(b) by 1010 days.

(21) Appl. No.: 17/631,995

(22) PCT Filed: Aug. 5, 2020

(86) PCT No.: PCT/US2020/045026

§ 371 (c)(1),
(2) Date: Feb. 1, 2022

(87) PCT Pub. No.: WO2021/026247

PCT Pub. Date: Feb. 11, 2021

(65) Prior Publication Data

US 2022/0273661 A1 Sep. 1, 2022

Related U.S. Application Data

(60) Provisional application No. 62/882,937, filed on Aug. 5, 2019.

(51) Int. Cl.
*A61K 31/519* (2006.01)
*A61P 39/00* (2006.01)

(52) U.S. Cl.
CPC ............ *A61K 31/519* (2013.01); *A61P 39/00* (2018.01)

(58) Field of Classification Search
CPC ......... A61P 39/00; A61P 43/00; A61K 31/519
See application file for complete search history.

(56) References Cited

U.S. PATENT DOCUMENTS

| | | | |
|---|---|---|---|
| 4,758,571 | A | 7/1988 | Curtius et al. |
| 4,774,244 | A | 9/1988 | Curtius et al. |
| 7,566,462 | B2 | 7/2009 | Jungles et al. |
| 7,566,714 | B2 | 7/2009 | Oppenheimer et al. |
| 7,582,799 | B2 | 9/2009 | Yoshino et al. |
| 7,612,073 | B2 | 11/2009 | Oppenheimer et al. |
| 7,727,987 | B2 | 6/2010 | Moser et al. |
| 7,732,599 | B2 | 6/2010 | Moser et al. |
| 7,947,681 | B2 | 5/2011 | Oppenheimer et al. |
| 8,003,126 | B2 | 8/2011 | Jungles et al. |
| 8,067,416 | B2 | 11/2011 | Oppenheimer et al. |
| 8,188,043 | B2 | 5/2012 | Cooke et al. |
| RE43,797 | E | 11/2012 | Oppenheimer et al. |
| 8,318,745 | B2 | 11/2012 | Moser et al. |
| 9,181,254 | B2 | 11/2015 | Yoshino et al. |
| 9,433,624 | B2 | 9/2016 | Oppenheimer et al. |
| 9,492,451 | B2 | 11/2016 | Rustomjee et al. |
| 9,993,481 | B2 | 6/2018 | Oppenheimer et al. |
| 11,072,614 | B2 | 7/2021 | Levy |
| 11,130,760 | B2 | 9/2021 | Yoshino et al. |
| 11,173,158 | B2 | 11/2021 | Hasegawa et al. |
| 2006/0040946 | A1 | 2/2006 | Oppenheimer et al. |
| 2007/0270581 | A1 | 11/2007 | Jungles et al. |
| 2008/0075666 | A1 | 3/2008 | Dudley et al. |
| 2010/0130500 | A1 | 5/2010 | Kakkis |
| 2011/0144117 | A1 | 6/2011 | Widmann et al. |
| 2013/0108694 | A1 | 5/2013 | Chou et al. |
| 2013/0237543 | A1 | 9/2013 | Oppenheimer et al. |
| 2015/0119574 | A1 | 4/2015 | Yoshino et al. |
| 2018/0078557 | A1 | 3/2018 | Hasegawa et al. |
| 2019/0308975 | A1 | 10/2019 | Levy |
| 2020/0009145 | A1 | 1/2020 | Hasegawa et al. |
| 2020/0010469 | A1 | 1/2020 | Yoshino et al. |
| 2020/0061070 | A1 | 2/2020 | Levy |
| 2021/0161901 | A1 | 6/2021 | Smith et al. |
| 2021/0220363 | A1 | 7/2021 | Smith et al. |
| 2021/0269443 | A1 | 9/2021 | Levy et al. |
| 2021/0300930 | A1 | 9/2021 | Levy |
| 2022/0081443 | A1 | 3/2022 | Yoshino et al. |

(Continued)

FOREIGN PATENT DOCUMENTS

| | | | |
|---|---|---|---|
| CN | 110354133 | A | 10/2019 |
| JP | 2008520574 | A | 6/2008 |

(Continued)

OTHER PUBLICATIONS

Berbée, M. (2011). Novel pharmacological strategies to reduce acute radiation injury. [Doctoral Thesis, Maastricht University]. Datawyse / Universitaire Pers Maastricht. https://doi.org/10.26481/dis.20111021mb (Year: 2011).*

Xue J, Yu C, Sheng W, et al. The Nrf2/GCH1/BH4 Axis Ameliorates Radiation-Induced Skin Injury by Modulating the ROS Cascade. J Invest Dermatol. 2017;137(10):2059-2068. doi:10.1016/j.jid.2017.05.019 (Year: 2017).*

Pannirselvam M, Simon V, Verma S, Anderson T, Triggle CR. Chronic oral supplementation with sepiapterin prevents endothelial dysfunction and oxidative stress in small mesenteric arteries from diabetic (db/db) mice. Br J Pharmacol. 2003;140(4):701-706. doi: 10.1038/sj.bjp.0705476 (Year: 2003).*

(Continued)

*Primary Examiner* — Sarah Pihonak
*Assistant Examiner* — Donna M Nestor
(74) *Attorney, Agent, or Firm* — Clark & Elbing LLP

(57) ABSTRACT

The invention provides methods for treating radiation exposure in a subject by administering sepiapterin, tetrahydrobiopterin, or dihydrobiopterin.

8 Claims, 25 Drawing Sheets

(56) References Cited

U.S. PATENT DOCUMENTS

| | | | |
|---|---|---|---|
| 2022/0362249 | A1 | 11/2022 | Smith |
| 2023/0110351 | A1 | 4/2023 | Smith |

FOREIGN PATENT DOCUMENTS

| | | | |
|---|---|---|---|
| TW | 200808320 | A | 2/2008 |
| WO | WO-2005/049000 | A2 | 6/2005 |
| WO | WO-2008/128049 | A2 | 10/2008 |
| WO | WO-2011/132435 | A1 | 10/2011 |
| WO | WO-2013/168693 | A1 | 11/2013 |
| WO | WO-2018/019931 | A1 | 2/2018 |
| WO | WO-2018/102314 | A1 | 6/2018 |
| WO | WO-2018/102315 | A1 | 6/2018 |
| WO | WO-2019/046849 | A1 | 3/2019 |
| WO | WO-2019/232120 | A1 | 12/2019 |
| WO | WO-2019/232126 | A1 | 12/2019 |
| WO | WO-2021/026247 | A1 | 2/2021 |
| WO | WO-2021/062264 | A1 | 4/2021 |
| WO | WO-2021/150983 | A1 | 7/2021 |
| WO | WO-2022/173823 | A1 | 8/2022 |
| WO | WO-2022/173834 | A1 | 8/2022 |
| WO | WO-2023/055923 | A1 | 4/2023 |

OTHER PUBLICATIONS

Berbee et al. Reduction of radiation-induced vascular nitrosative stress by the vitamin E analog γ-tocotrienol: evidence of a role for tetrahydrobiopterin. Int J Radiat Oncol Biol Phys. Mar. 1, 2011;79(3): 884-91. doi: 10.1016/j.ijrobp.2010.08.032. Epub Oct. 1, 20103. PMID: 20950957; PMCID: PMC3023840. (Year: 2010).*

Sawabe et al. (2002). Sepiapterin Administration Raises Tissue BH4 Levels More Efficiently Than BH4 Supplement in Normal Mice. In: Milstien et al (eds) Chemistry and Biology of Pteridines and Folates. Springer, Boston, MA. https://doi.org/10.1007/978-1-4615-0945-5_33 (Year: 2002).*

Akleyev, A.V. (2014). Definition, Classification, and Clinical Presentation of Chronic Radiation Syndrome (CRS) Associated with Total Exposure to External Radiation. In: Chronic Radiation Syndrome. Springer, Berlin, Heidelberg. https://doi.org/10.1007/978-3-642-45117-1_1 (Year: 2014).*

Bruno, N. "Normalizing Tumor Vasculature Using Sepiapterin to Increase Radiosensitivity," Thesis, Virginia Commonwealth University (Nov. 2015) (45 pages).

Abell et al., "Effect of oral CNSA-001 (sepiapterin, PTC923) on gastric accommodation in women with diabetic gastroparesis: a randomized, placebo-controlled, phase 2 trial," J Diabetes Complications. 35(9):107961 (2021) (7 pages).

Almudéver et al., "Role of tetrahydrobiopterin in pulmonary vascular remodelling associated with pulmonary fibrosis," Thorax. 68(10):938-948 (2013).

Berbée et al., "Novel strategies to ameliorate radiation injury: a possible role for tetrahydrobiopterin." Curr Drug Targets. 11(11): 1366-1374 (2010).

Bernegger et al., "High frequency of tetrahydrobiopterin-responsiveness among hyperphenylalaninemias: a study of 1,919 patients observed from 1988 to 2002," Mol Genet Metab. 77(4):304-13 (2002).

Blau et al., "Tetrahydrobiopterin deficiencies without hyperphenylalaninemia: diagnosis and genetics of DOPA-responsive dystonia and sepiapterin reductase deficiency," Mol Genet Metab. 74(1-2):172-85 (2001).

Bratkovic et al., "PTC923 (sepiapterin) lowers elevated blood phenylalanine in subjects with phenylketonuria: a phase 2 randomized, multi-center, three-period crossover, open-label, active controlled, all-comers study," Metabolism. 128:155116 (2022) (8 pages).

Cardnell et al., "Sepiapterin Ameliorates Chemically Induced Murine Colitis and Azoxymethane-Induced Colon Cancer," J Pharmacol Exp Ther. 347(1):117-125 (2013).

ClinicalTrials.gov Identifier: NCT03519711, "A Study of CNSA-001 in Primary Tetrahydrobiopterin (BH4) Deficient Participants with Hyperphenylalaninemia," <https://clinicaltrials.gov/ct2/show/study/NCT03519711>, first posted May 9, 2018, last updated Jan. 5, 2021, retrieved on Feb. 11, 2021 (5 pages).

Cronin et al., "The metabolite BH4 controls T-cell proliferation in autoimmunity and cancer," available in PMC Mar. 28, 2019, published in final edited form as: Nature. 563(7732):564-568 (2018) (44 pages).

Curtius et al., "Atypical phenylketonuria due to tetrahydrobiopterin deficiency. Diagnosis and treatment with tetrahydrobiopterin, dihydrobiopterin and sepiapterin." Clin Chim Acta. 93(2):251-62 (1979).

Grant et al., "Relationships among rat ultrasonic vocalizations, behavioral measures of striatal dopamine loss, and striatal tyrosine hydroxylase immunoreactivity at acute and chronic time points following unilateral 6-hydroxydopamine-induced dopamine depletion," available in PMC Sep. 15, 2016, published in final edited form as: Behav Brain Res. 291:361-71 (2015) (24 pages).

Hennermann et al., "Partial and total tetrahydrobiopterin-responsiveness in classical and mild phenylketonuria (PKU)," J Inherit Metab Dis. 25(Suppl 1):21:041-P (2002) (Abstract only).

Ichiyama et al., "Enzymic studies on the biosynthesis of serotonin in mammalian brain," J Biol Chem. 245(7):1699-709 (1970).

International Search Report and Written Opinion for International Application No. PCT/US2020/045026, mailed Oct. 15, 2020 (15 pages).

Kaufman, "Phenylalanine hydroxylation cofactor in phenylketonuria," Science. 128(3337):1506-8 (1958).

Klaiman et al., "Tetrahydrobiopterin as a treatment for autism spectrum disorders: a double-blind, placebo-controlled trial," J Child Adolesc Psychopharmacol. 23(5):320-8 (2013) (11 pages).

Kuplennik et al., "Enhanced nanoencapsulation of sepiapterin within PEG-PCL nanoparticles by complexation with triacetyl-beta cyclodextrin," Molecules. 24(15):2715 (Jul. 2019) (19 pages).

Kure et al., "Tetrahydrobiopterin-responsive phenylalanine hydroxylase deficiency," J Pediatr. 135(3):375-8 (1999).

Kuznetsova et al., "Nitric Oxide: Properties, Biological Role, Mechanisms of Action," Modern Problems of Science and Education. 4, <https://science-education.ru/ru/article/view?id=21037>, published Jul. 31, 2015, retrieved Jan. 17, 2023 (machine-generated English translation included) (21 pages).

Kwon et al., "Reduced biopterin as a cofactor in the generation of nitrogen oxides by murine macrophages," J Biol Chem. 264(34):20496-501 (1989).

Matalon et al., "Tetrahydrobiopterin (BH4) responsive phenylalanine hydroxylase (PAH) mutations," J Inherit Metab Dis. 25(Suppl 1):23:045-P (2002) (Abstract only).

Mayer et al., "Brain nitric oxide snythase is a biopterin- and flavin-containing multi-functional oxido-reductase," FEBS Lett. 288(1-2):187-91 (1991).

Mikkelsen et al., "Oral sepiapterin mitigates radiation induced lung and heart toxicity," Radiation Research Society 65th Annual Meeting, Nov. 3-6, San Diego, CA. Abstract (2019).

Muntau et al., "Tetrahydrobiopterin as an alternative treatment for mild phenylketonuria," N Engl J Med. 347(26):2122-32 (2002).

Nagatsu et al., "Tyrosine hydroxylase. The initial step in norepinephrine biosynthesis," J Biol Chem. 239(9):2910-7 (1964).

Niederwieser et al., "Atypical phenylketonuria with defective biopterin metabolism. Monotherapy with tetrahydrobiopterin or sepiapterin, screening and study of biosynthesis in man," Eur J Pediatr. 138(2):110-2 (1982).

Opladen et al., "Consensus guideline for the diagnosis and treatment of tetrahydrobiopterin (BH4) deficiencies." Orphanet J Rare Dis. 15(1):126 (May 2020) (30 pages).

Park et al., "Optimization of expression conditions enhances production of sepiapterin, a precursor for tetrahydrobiopterin biosynthesis, in recombinant *Escherichia coli*," J Microbiol Biotechnol. 25(10):1709-13 (2015) (5 pages).

Pfleiderer, "Pteridine, LXVIII. Überführung von biopterin in sepiapterin und absolute konfiguration des sepiapterins," Chem Ber. 112:2750-2755 (1979).

(56) References Cited

OTHER PUBLICATIONS

Ponzone et al., "Hyperphenylalaninemia and pterin metabolism in serum and erythrocytes," Clin Chim Acta. 216(1-2):63-71 (1993).
Rabender et al., "Mitigation of Radiation-Induced Lung and Heart Injuries in Mice by Oral Sepiapterin after Irradiation," available in PMC May 1, 2022, published in final edited form as: Radiat Res. 195(5):463-473 (2021) (20 pages).
Rabender et al., "Sepiapterin Enhances Tumor Radio- and Chemosensitivities by Promoting Vascular Normalization," J Pharmacol Exp Ther. 365(3):536-543 (2018).
Rabender et al., "The Role of Nitric Oxide Synthase Uncoupling in Tumor Progression," Mol Cancer Res. 13(6):1034-1043 (2015) (11 pages).
Sawabe et al., "Cellular uptake of sepiapterin and push-pull accumulation of tetrahydrobiopterin," Mol Genet Metab. 94(4):410-6 (2008).
Sawabe et al., Sepiapterin administration raises tissue BH4 levels more efficiently than BH4 supplement in normal mice, *Chemistry and Biology of Pteridines and Folates*. Ed. Milstien et al., pp. 199-204 (2001).
Schircks et al., "Herstellung von (6 R,S)-5,6,7,8-Tetrahydro-L-biopterin, 7,8-Dihydro-L-biopterin, L-Sepiapterin, Deoxysepiapterin, (6 R,S)-5,6-Dihydrodeoxysepiapterin und 2'-Deoxybiopterin," Helvetica Chimica Acta. 61(7):2731-2738 (1978).
Schircks et al., "Über Pterinchemie. 65 Mitteilung [1]. Herstellung von (6 R,S)-5,6,7,8-Tetrahydro-L-biopterin, 7,8-Dihydro-L-biopterin, L-Sepiapterin, Deoxysepiapterin, (6 R,S)-5,6-Dihydrodeoxysepiapterin and 2'-Deoxybiopterin," Helv Chim Acta. 61(7):2731-8 (1978).
Shimazu et al., "Sepiapterin enhances angiogenesis and functional recovery in mice after myocardial infarction," Am J Physiol Heart Circ Physiol. 301(5):H2061-H2072 (2011).
Schircks Laboratories, "Data Sheet: L-Sepiapterin. Product No. 11.225," published Jan. 26, 2016 (1 page).
Schircks Laboratories, "Data Sheet: Tetrahydrobiopterin Tablets," published Jul. 1, 2009 (1 page).
Smith et al., "Exploratory study of the effect of one week of orally administered CNSA-001 (sepiapterin) on CNS levels of tetrahydrobiopterin, dihydrobiopterin and monoamine neurotransmitter metabolites in healthy volunteers," Mol Genet Metab Rep. 21:100500 (Dec. 2019) (3 pages).
Smith et al., "Phase I clinical evaluation of CNSA-001 (sepiapterin), a novel pharmacological treatment for phenylketonuria and tetrahydrobiopterin deficiencies, in healthy volunteers," Mol Genet Metab. 126(4):406-12 (Feb. 2019).
Spaapen et al., "Tetrahydrobiopterin-responsive phenylalanine hydroxylase deficiency, state of the art," Mol Genet Metab. 78(2):93-9 (2003).
Sugiura et al., "The structures of the reoxidation products of 7,8-dihydroneopterin," Bull Chem Soc Jpn. 46(3):939-42 (1973).
"Tetrahydrobiopterin Deficiency," NORD, <https://web.archive.org/web/20160901103424/https://rarediseases.org/rare-diseases/tetrahydrobiopterin-deficiency/>, last updated Sep. 1, 2016, retrieved Feb. 11, 2021 (10 pages).
Tietz et al., "A new pteridine-requiring enzyme system for the oxidation of glyceryl ethers," J Biol Chem. 239(12):4081-90 (1964).
Viscontini et al., "Fluoreszierende Stoffe aus Drosophila melanogaster. 12. Mitteilung. Die gelb fluoreszierenden Pterine: Sepiapterin und Isosepiapterin," Helvetica Chimica Acta. 42:836-41 (1959) (7 Pages).
Woo et al., "Production of sepiapterin in *Escherichia coli* by coexpression of cyanobacterial GTP cyclohydrolase I and human 6-pyruvoyltetrahydropterin synthase," Appl Environ Microbiol. 68(6):3138-3140 (2002).
Yan et al., "Ionizing radiation induces BH4 deficiency by downregulating GTP-cyclohydrolase 1, a novel target for preventing and treating radiation enteritis." Biochemical Pharmacology. 180: 114102 (Jun. 2020) (10 pages).
Zhang et al., "Tetrahydrobiopterin protects against radiation-induced growth inhibition in H9c2 cardiomyocytes." Chin Med J (Engl). 129(22):2733-2740 (2016).
Zheng et al., "Correction of arginine metabolism with sepiapterin-the precursor of nitric oxide synthase cofactor BH4-induces immunostimulatory-shift of breast cancer," available in PMC Jan. 28, 2021, published in final edited form as: Biochem Pharmacol. 176:113887 (Jun. 2020) (24 pages).

* cited by examiner

- Non-invasive measurements: Echocardiography, breathing rate, weight, CT at baseline and days 10, 30, 90 180 post RT, n = 15/ group per each time point.
- Molecular and Immunohistochemical analysis: baseline and days 10, 30, 90 and 180 post RT

*p<0.05 vs baseline

#p<0.05 vs vehicle 10d, p<0.05vs vehicle 30d, p<0.05 vs vehicle 60d, p<0.05 vs vehicle 90d, @p<0.05 vs vehicle.

*$p<0.05$ vs baseline

#$p<0.05$ vs vehicle 10d, $p<0.05$vs vehicle 30d, $p<0.05$ vs vehicle 60d, $p<0.05$ vs vehicle 90d, @$p<0.05$ vs vehicle.

IR-inhibited exosomal miRNA

IR-Induced exosomal miRNA

FIG. 12

| | | | Relative expression | | | | | |
|---|---|---|---|---|---|---|---|---|
| group | # | Fibrosis | Ccl2 | Runx2 | IL-1beta | IL-6 | IL-17a |
| IR + Vehicle | M1 | 2.97 | 1.43 | 0.29 | 3.32 | 21.65 | 3.74 |
| | M2 | 3.32 | 0.83 | 1.06 | 3.10 | 22.98 | 3.68 |
| | M3 | [illegible] | [illegible] | [illegible] | [illegible] | [illegible] | [illegible] |
| | M4 | [illegible] | [illegible] | [illegible] | [illegible] | [illegible] | [illegible] |
| | F1 | [illegible] | [illegible] | [illegible] | [illegible] | [illegible] | [illegible] |
| IR + SP | M1 | [illegible] | [illegible] | [illegible] | [illegible] | [illegible] | [illegible] |
| | M2 | 2.17 | 1.37 | 0.68 | 2.93 | 13.80 | 1.36 |
| | M3 | 1.33 | 1.06 | 0.43 | 2.81 | 15.10 | 1.37 |
| | M5 | 1.69 | 1.75 | 0.52 | 3.06 | 12.17 | 1.44 |
| | F1 | 1.51 | 1.97 | 0.54 | 3.13 | 17.50 | 1.16 |
| | F2 | [illegible] | [illegible] | [illegible] | [illegible] | [illegible] | [illegible] |

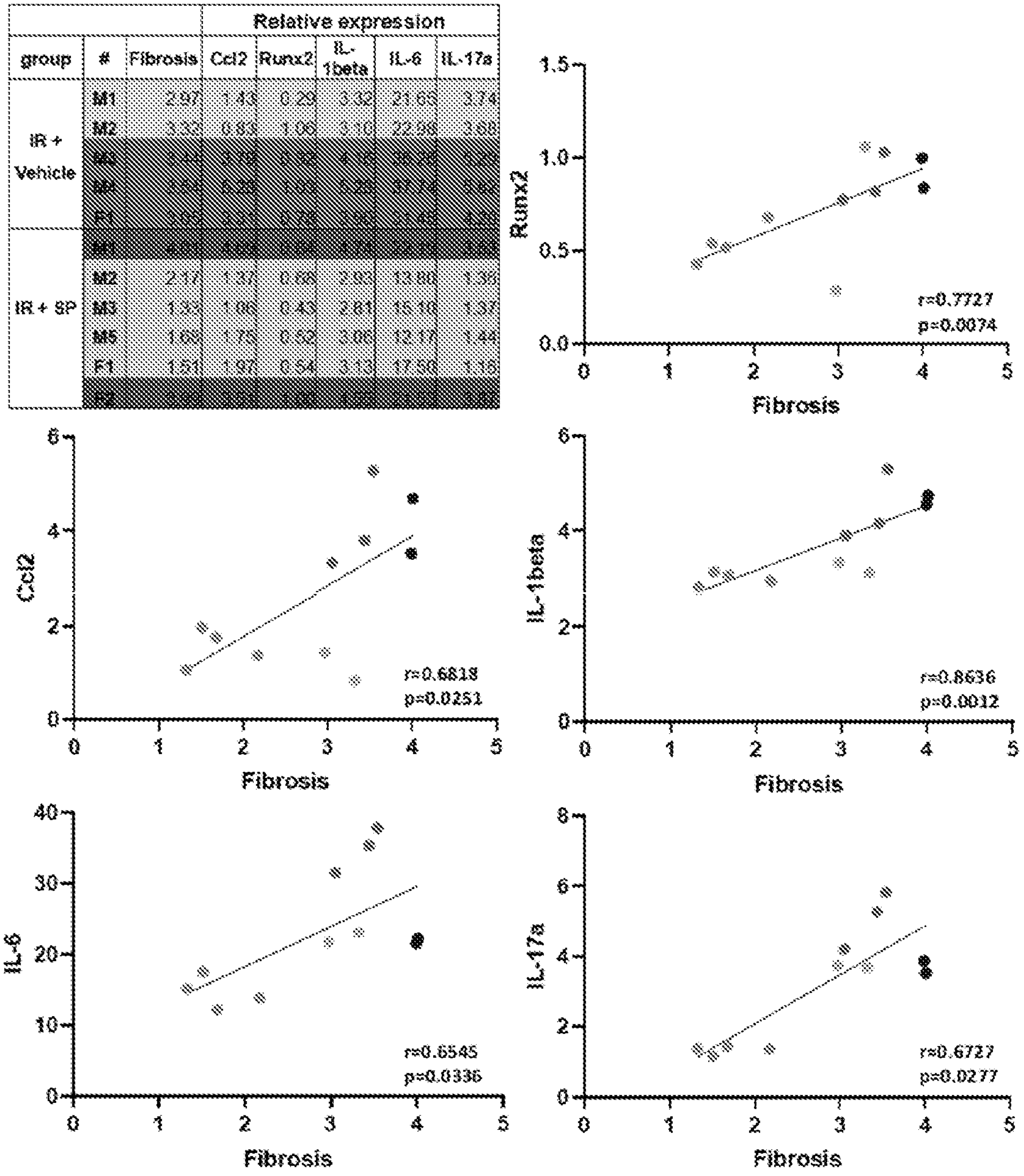

| | | | Relative expression | | | | | |
|---|---|---|---|---|---|---|---|---|
| group | # | Fibrosis | Ctgf | BMP2 | Spp2 | TGF-beta 1 | IL-10 | Trim72 |
| IR + Vehicle | M1 | 2.97 | 0.48 | 0.69 | 3.74 | 3.16 | 0.39 | 1.94 |
| | M2 | 3.32 | 0.57 | 0.46 | 3.73 | 3.00 | 0.38 | 1.19 |
| | M3 | 3.44 | 0.71 | 0.79 | 3.97 | 3.85 | 0.60 | 0.51 |
| | M4 | 3.54 | 1.40 | 0.94 | 4.86 | 2.91 | 0.47 | 0.57 |
| | F1 | 3.03 | 0.77 | 0.82 | 4.93 | 3.43 | 0.41 | 0.24 |
| IR + SP | M1 | 4.00 | 0.79 | 0.81 | 2.71 | 1.88 | 0.67 | 0.47 |
| | M2 | 2.17 | 0.99 | 1.16 | 2.21 | 1.99 | 0.62 | 1.24 |
| | M3 | 1.33 | 0.75 | 0.55 | 2.52 | 1.32 | 0.40 | 0.47 |
| | M5 | 1.68 | 0.91 | 0.49 | 2.38 | 1.34 | 0.48 | 1.01 |
| | F1 | 1.51 | 0.57 | 0.26 | 2.31 | 1.44 | 0.36 | 0.22 |
| | F2 | 4.00 | 1.11 | 0.61 | 2.14 | 2.17 | 0.74 | 0.85 |

** - *p-value* < 0.05; *** - *p-value* < 0.001

** - *p-value* < 0.05; *** - *p-value* < 0.001

Tei index vehicle

□ = female
▨ = male baseline
IR 10 days
IR 10 days
IR 30 days
IR 30 days
IR 60 days
IR 60 days
IR 90 days
IR 90 days
IR 180 days
IR 180 days

USE OF SEPIAPTERIN AND METABOLITES THEREOF TO TREAT RADIATION EXPOSURE

STATEMENT AS TO FEDERALLY SPONSORED RESEARCH

This invention was made with government support under Grant Number R01 AI133595 awarded by the National Institutes of Health (NIH). The government has certain rights in the invention.

BACKGROUND OF THE INVENTION

Whether through an act of terrorism or a nuclear accident, the threat of a radiological disaster represents a potentially catastrophic public health emergency underscoring the need for the development of medical countermeasures to mitigate total body radiation-induced injuries and mortalities. The initial health consequence of a total body radiation (TBI) exposure is an acute radiation syndrome (ARS) in the most radiosensitive organs, with survival from this exposure being dictated by the extent of damage to stem and progenitor cells in the hematopoietic system as well as the epithelium in the gastrointestinal system. Hematopoietic growth factors, electrolytes and fluids, blood transfusions and antibiotics are all advancements in therapies to treat ARS that have resulted in significant improvements in survival. However, as seen with survivors of Chernobyl, patients surviving the ARS to the Hematopoietic and GI systems often succumb to late injury in the lung and heart.

Accordingly, there is a need for treatments that improve mortality rates and organ function in patients exposed to radiation.

SUMMARY OF THE INVENTION

The present invention features methods for the treatment of patients with radiation exposure. For example, the present invention employs sepiapterin (SP) to mitigate toxicity to the heart, gastrointestinal tract, and/or lungs of the patient.

In one aspect, the invention provides a method of treating a subject exposed to radiation by administering an effective amount of sepiapterin, tetrahydrobiopterin, or dihydrobiopterin or a pharmaceutically acceptable salt or co-crystal thereof to the subject.

In certain embodiments, the administering reduces or inhibits tissue and/or organ damage in the subject; reduces or inhibits cardiac, gastrointestinal, and/or lung toxicity in the subject; decreases gastrointestinal, cardiac, and/or lung endothelial cell death in the subject; and/or reduces radiation-induced inflammation in gastrointestinal, cardiac, and/or lung epithelial cells in the subject.

The effective amount is, for example, from about 0.1 to about 200 mg/kg/day, e.g., about 5 mg/kg/day to about 35 mg/kg/day.

In embodiments, the subject has acute radiation syndrome, e.g., with the administering occurring within 24 hours after exposure to radiation. In embodiments, the subject has chronic radiation syndrome. In embodiments, the subject has cutaneous radiation syndrome. In embodiments, the subject is exposed to at least 0.3 Gy in less than one day. In embodiments, the subject is exposed to at least 0.7 Gy over a period of more than one day.

In embodiments, the administering occurs at least once daily for at least six days, e.g., at least one week, at least 10 days (e.g., at least 14 days), at least about one month, at least about three months, at least about six months, at least about nine months, or at least about one year.

In embodiments, the administering increases expression of miR-15b-3p, miR-106a-5p, miR-133b, miR-136-5p, miR-451a, miR-1, miR-335-3p, let-7d-3p, and/or let-7c-5p, e.g., serum exosomal (e.g., when BH4 is administered), and/or decreases the expression of IL-1β, IL-6, IL-17A, Spp2, and/or TGF-β1 in lung epithelial cells (e.g., when SP is administered). In embodiments, the administering increases expression of let-7a-5p, miR-1, miR-106b-3p, miR-106b-5p, miR-126-3p, miR-181a-5p, miR-335-3p, and/or miR-335-5p and/or decreases expression of let-7g-5p, let-7i-5p, and/or miR-16-5p, e.g., serum exosomal (e.g., when SP is administered).

In one aspect, the invention features a method of reducing or inhibiting tissue and/or organ damage in a subject that has been exposed to radiation by administering to the subject an effective amount of sepiapterin or a pharmaceutically acceptable salt thereof.

In another aspect, the invention features a method of reducing or inhibiting cardiac and/or lung toxicity in a subject that has been exposed to radiation by administering to the subject an effective amount of sepiapterin or a pharmaceutically acceptable salt thereof.

In another aspect, the invention features a method of decreasing cardiac and/or lung endothelial cell death in a subject that has been exposed to radiation by administering to the subject an effective amount of sepiapterin or a pharmaceutically acceptable salt thereof.

In another aspect, the invention features a method of reducing radiation-induced inflammation in cardiac and/or lung epithelial cells in a subject by administering to the subject an effective amount of sepiapterin or a pharmaceutically acceptable salt thereof.

In one embodiment of the preceding four aspects, the effective amount of sepiapterin or pharmaceutically acceptable salt thereof is less than 1 mg/kg.

In another embodiment of the preceding four aspects, the sepiapterin or pharmaceutically acceptable salt thereof is administered about 24 hours after exposure to radiation.

In another embodiment of the preceding four aspects, the method includes administering sepiapterin or pharmaceutically acceptable salt thereof in multiple doses.

In another embodiment of the preceding four aspects, the method includes administering sepiapterin or pharmaceutically acceptable salt thereof daily for at least six days.

In another embodiment of the preceding four aspects, the effective amount of sepiapterin or pharmaceutically acceptable salt thereof results in an increase in expression of miR-15b-3p, miR-106a-5p, miR-133b, miR-136-5p, miR-451a, miR-1, miR-335-3p, let-7d-3p, and/or let-7c-5p.

Definitions

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

In some embodiments, the term "about," as used herein means±10% of the specified value.

Reference to "about" or "approximately" a value or parameter herein includes (and describes) variations that are directed to that value or parameter per se. For example, description referring to "about X" includes description of "X".

As used herein, the term "administration" refers to the administration of a composition to a subject. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal, or vitreal.

An "effective amount" of a compound may vary according to factors such as the disease state, age, sex, and weight of the individual, and the ability of the compound to elicit the desired response. A therapeutically effective amount encompasses an amount in which any toxic or detrimental effects of the compound are outweighed by the therapeutically beneficial effects. A therapeutically effective amount also encompasses an amount sufficient to confer benefit, e.g., clinical benefit.

By "level" is meant a level of a compound, as compared to a reference. The reference can be any useful reference, as defined herein. By a "decreased level" or an "increased level" of a compound is meant a decrease or increase in compound level, as compared to a reference (e.g., a decrease or an increase by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 150%, at least about 200%, at least about 300%, at least about 400%, at least about 500%, or more; a decrease or an increase by less than about 0.01-fold, less than about 0.02-fold, less than about 0.1-fold, less than about 0.3-fold, less than about 0.5-fold, less than about 0.8-fold, or less; or an increase by more than about 1.2-fold, more than about 1.4-fold, more than about 1.5-fold, more than about 1.8-fold, more than about 2.0-fold, more than about 3.0-fold, more than about 3.5-fold, more than about 4.5-fold, more than about 5.0-fold, more than about 10-fold, more than about 15-fold, more than about 20-fold, more than about 30-fold, more than about 40-fold, more than about 50-fold, more than about 100-fold, more than about 1000-fold, or more). A level of a compound may be expressed in mass/vol (e.g., g/dL, mg/mL, μg/mL, ng/mL) or percentage relative to total compound in a sample.

The term "pharmaceutical composition," as used herein, represents a composition containing a compound described herein formulated with a pharmaceutically acceptable excipient. A pharmaceutical composition may be one manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gel cap, powder for suspension, suspension, solution, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation.

As used herein, the term "pharmaceutically acceptable salt" means any pharmaceutically acceptable salt of sepiapterin, tetrahydrobiopterin, or dihydrobiopterin. Pharmaceutically acceptable salts include ion pairs of sepiapterin, tetrahydrobiopterin, or dihydrobiopterin in the solid state and/or in solution. A pharmaceutically acceptable co-crystal includes freebase sepiapterin, tetrahydrobiopterin, or dihydrobiopterin and an acid in a solid state. Mixture of the salt form and co-crystal form may be present in the same composition. For example, pharmaceutically acceptable salts of sepiapterin, tetrahydrobiopterin, or dihydrobiopterin include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: in Remington (Remington: The Science and Practice of Pharmacy, (22nd ed.) ed. L. V. Allen, Jr., 2013, Pharmaceutical Press, Philadelphia, PA). The salts can be prepared in situ during the final isolation and purification of the compounds described herein or separately by reacting a free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts.

By a "reference" is meant any useful reference used to compare compound levels or other symptoms, e.g., tissue and/or organ damage, toxicity cell, death, or inflammation. The reference can be any sample, standard, standard curve, or level that is used for comparison purposes. The reference can be a normal reference sample or a reference standard or level. A "reference sample" can be, for example, a control, e.g., a predetermined negative control value such as a "normal control" or a prior sample taken from the same subject; a sample from a normal healthy subject, such as a normal cell or normal tissue; a sample (e.g., a cell or tissue) from a subject not having a disease; a sample from a subject that is diagnosed with a disease, but not yet treated with a compound of the invention; a sample from a subject that has been treated by a compound of the invention; or a sample of a purified compound (e.g., any described herein) at a known normal concentration. By "reference standard or level" is meant a value or number derived from a reference sample. A "normal control value" is a pre-determined value indicative of non-disease state, e.g., a value expected in a healthy control subject. Typically, a normal control value is expressed as a range ("between X and Y"), a high threshold ("no higher than X"), or a low threshold ("no lower than X"). A subject having a measured value within the normal control value for a particular biomarker is typically referred to as "within normal limits" for that biomarker. A normal reference standard or level can be a value or number derived from a normal subject not having a disease or disorder (e.g., ARS). In preferred embodiments, the reference sample, standard, or level is matched to the subject sample by at least one of the following criteria: age, weight, sex, disease stage, and overall health. A standard curve of levels of a purified compound, e.g., any described herein, within the normal reference range can also be used as a reference.

As used herein, the term "subject" or "patient" refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the terms "treat," "treated," or "treating" mean both therapeutic treatment and prophylactic or preventative measures wherein the object is to prevent or slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment.

It is to be understood that the description of compounds, compositions, formulations, and methods of treatment described herein include "comprising", "consisting of", and "consisting essentially of" embodiments. In some embodiments, for all compositions described herein, and all methods using a composition described herein, the compositions can either comprise the listed components or steps, or can "consist essentially of" the listed components or steps. When a composition is described as "consisting essentially of" the listed components, the composition contains the components listed, and may contain other components which do not substantially affect the condition being treated, but do not contain any other components which substantially affect the condition being treated other than those components expressly listed; or, if the composition does contain extra components other than those listed which substantially affect the condition being treated, the composition does not contain a sufficient concentration or amount of the extra components to substantially affect the condition being treated. When a method is described as "consisting essentially of" the listed steps, the method contains the steps listed, and may contain other steps that do not substantially affect the condition being treated, but the method does not contain any other steps which substantially affect the condition being treated other than those steps expressly listed. As a non-limiting specific example, when a composition is described as 'consisting essentially of' a component, the composition may additionally contain any amount of pharmaceutically acceptable carriers, vehicles, or diluents and other such components which do not substantially affect the condition being treated.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the description below. Other features, objects, and advantages of the invention will be apparent from the description and from the claims.

DETAILED DESCRIPTION OF THE INVENTION

Figure 1:
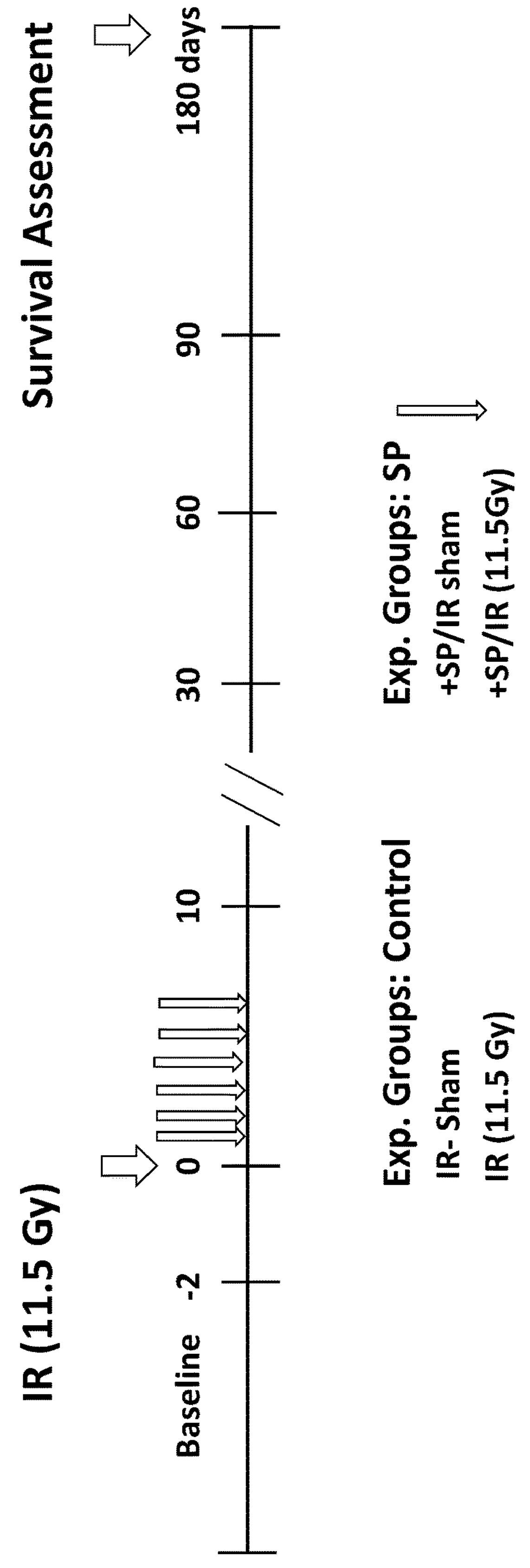
FIG. 1 illustrates the experimental protocol used in the present invention. Experimental groups were treated with radiation followed by tetrahydrobiopterin (BH4), sepiapterin (SP), or vehicle, and assessed at 10, 30, 60, 90, and 180 days after radiation treatment.

The present invention features methods of use of sepiapterin, tetrahydrobiopterin, dihydrobiopterin or a pharmaceutically acceptable salt or co-crystal thereof to treat subjects exposed to radiation. Without wishing to be bound by theory, we believe that radiation-induced late lung, gastrointestinal, and heart toxicities are a consequence of endothelial dysfunction defined as uncoupled NOS activity and decreased NO bioavailability establishing a state of chronic inflammation driving a persistent pro-fibrotic process associated with abnormal wound repair and late normal tissue injury. In a murine model with similar radiosensitivity to humans, we show that sepiapterin and metabolites thereof, such as tetrahydrobiopterin and dihydrobiopterin, can be used as a radiation countermeasure to mitigate radiation-induced cardiac and pulmonary injury and improve survival.

Active Compounds

The methods of the invention feature use of sepiapterin, tetrahydrobiopterin, or dihydrobiopterin, or a salt and/or co-crystal thereof. Sepiapterin can convert into dihydrobiopterin and tetrahydrobiopterin in vivo, and dihydrobiopterin and tetrahydrobiopterin interconvert in vivo.

Sepiapterin has the structure:

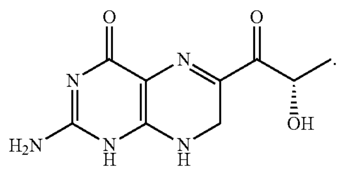 [SMILES: C[C@H](O)C(=O)C1=Nc2c([nH]c(N)nc2=O)NC1]

Tetrahydrobiopterin has the structure:

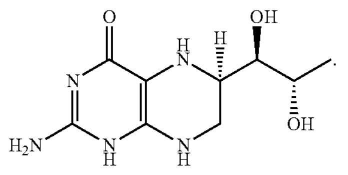 [SMILES: C[C@H](O)[C@H](O)[C@H]1CNc2[nH]c(N)nc(=O)c2N1]

Dihydrobiopterin has the structure:

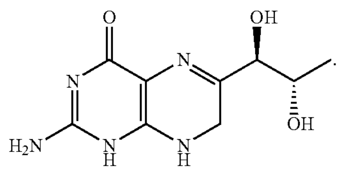 [SMILES: C[C@H](O)[C@H](O)C1=Nc2c([nH]c(N)nc2=O)NC1]

The active compound may be employed in any suitable form, e.g., free base, salt, or co-crystal. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, gentisate, glucoheptonate, glycerophosphate, glycolate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. In some embodiments, the active compound or salt thereof is in a crystalline form.

Exemplary salts, co-crystals, and crystalline forms of sepiapterin are described in WO 2018/102314, WO 2018/102315, WO 2019/046849, and WO 2019/232120, e.g., any of crystalline Forms A, B, C, D, E, F, or G described in WO 2018/102314 or WO 2018/102315. Other salts or crystal forms of sepiapterin, dihydrobiopterin, and/or tetrahydrobiopterin are known in the art.

Methods of Treatment

The invention provides methods of treating a subject after radiation exposure, e.g., in the treatment of acute radiation syndrome (ARS), cutaneous radiation syndrome, or chronic radiation syndrome. In particular, the invention provides methods of treating exposure of a patient to at least about 0.05 Gy in a period of less than 24 hours. For example, the patient may have been exposed to at least about 0.3, at least about 0.7, at least about 1, at least about 3, at least about 5, at least about 6, at least about 8, at least about 10, at least about 15, at least about 20, at least about 30, or at least about 50 Gy, such as between about 0.3 and about 6, between about 0.7 and about 6, between about 1 and about 2, between about 2 and about 6, between about 6 and about 20, between about 6 and about 10, between about 6 and about 8, between about 10 and about 20, between about 8 and about 12, or between about 20 and about 50 Gy, and the period of exposure may be less than about 18 hours, e.g., less than about 12, less than about 6, less than about 3, less than about 1, less than about 0.5, or less than about 0.1 h or less than about 5, less than about 3, less than about 2, or less than about 1 min. Alternatively, the invention provides methods of treating exposure of a patient to at least about 0.7 Gy over a period of greater than 24 hours. For example, the patient may have been exposed to at least about 0.7, at least about 1, at least about 2, at least about 3, at least about 4, at least about 5, at least about 6, at least about 7, or at least about 8 Gy, and the period of exposure may be at least about one week, at least about one month, at least about three months, at least about 6 months, at least about 9 months, at least about 1 year, at least about 2 years, at least about 3 years, or more, e.g., from about 1 week to 3 years, about 1 week to 1 year, about 1 week to 1 month, about 1 month to 2 years, about 1 month to 1 year, about 6 months to 2 years, about 9 months to 2 years, or about 9 months to 15 months. The radiation exposure may be whole body or localized, e.g., to the skin. In certain embodiments, the radiation does not result from radiotherapy.

Treatment according to the invention may result in reducing or inhibiting tissue and/or organ damage in a subject that has been exposed to radiation; reducing or inhibiting tissue or organ toxicity, e.g., lung, heart, or gastrointestinal, such as lung or heart, in a subject that has been exposed to radiation; decreasing endothelial cell death, e.g., lung, heart, or gastrointestinal, such as lung or heart, in a subject that has been exposed to radiation; reducing radiation-induced inflammation in epithelial cells, e.g., lung, heart, or gastrointestinal, such as lung or heart, in a subject; increasing expression of miR-15b-3p, miR-106a-5p, miR-133b, miR-136-5p, miR-451a, miR-1, miR-335-3p, let-7d-3p, and/or let-7c-5p; reducing expression of IL-1β, IL-6, IL-17A, Spp2, and/or TGF-β1, e.g., in lung epithelial cells; increasing expression of let-7a-5p, miR-1, miR-106b-3p, miR-106b-5p, miR-126-3p, miR-181a-5p, miR-335-3p, and/or miR-335-5p; and/or decreasing expression of let-7g-5p, let-7i-5p, and/or miR-16-5p. Reduction in symptoms or cytokines may be by at least about 5%, at least about 10%, at least about 20%, at least about 30%, at least about 40%, at least about 50%, at least about 60%, at least about 70%, at least about 80%, at least about 90%, or at least about 95%, e.g., relative to a reference. Increase in oligonucleotide expression may be by at least about 5%, at least about 10%, at least about 20%, at least about 30%, at least about 40%, at least about 50%, at least about 60%, at least about 70%, at least about 80%, at least about 90%, at least about 95%, at least about 100%, at least about 200%, at least about 300%, or at least about 500%, e.g., relative to a reference.

The active compound can be administered in any suitable dose. The actual dosage amount of a composition of the present invention administered to a patient can be determined by physical and physiological factors such as body weight, severity of condition, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject. A therapeutically effective amount may be from about 0.1 mg/kg/day to about 200 mg/kg/day, e.g., about 0.1 to about 150 mg/kg/day, about 0.1 to about 125 mg/kg/day, about 0.1 to about 100 mg/kg/day, about 0.1 to about 80 mg/kg/day, about 0.1 to about 60 mg/kg/day, about 0.1 to about 40 mg/kg/day, about 0.1 to about 25 mg/kg/day, about 0.1 to about 20 mg/kg/day, about 0.1 to about 15 mg/kg/day, about 0.1 to about 10 mg/kg/day, about 0.1 to about 5 mg/kg/day, about 0.1 to about 2.5 mg/kg/day, about 0.1 to about 1 mg/kg/day, about 0.1 to about 0.5 mg/kg/day, about 0.5 to about 200 mg/kg/day, about 1 to about 200 mg/kg/day, about 2.5 to about 200 mg/kg/day, about 5 to about 200 mg/kg/day, about 10 to about 200 mg/kg/day, about 15 to about 200 mg/kg/day, about 20 to about 200 mg/kg/day, about 25 to about 200 mg/kg/day, about 40 to about 200 mg/kg/day, about 60 to about 200 mg/kg/day, about 80 to about 200 mg/kg/day, about 100 to about 200 mg/kg/day, about 120 to about 200 mg/kg/day, about 140 to about 200 mg/kg/day, about 160 to about 200 mg/kg/day, about 180 to about 200 mg/kg/day, about 5 to 1 about 80 mg/kg/day, about 10 to about 160 mg/kg/day, about 20 to about 140 mg/kg/day, about 40 to about 120 mg/kg/day, about 60 to about 100 mg/kg/day, about 5 to about 50 mg/kg/day, or about 10 to about 20 mg/kg/day of active compound. Administration may occur any suitable number of times, e.g., once daily, twice daily or three times daily during treatment. Administration may continue for as long as necessary, e.g., from one day to about one year or at least 6 days, at least about one week, at least about two weeks, at least about one month, at least about three months, at least about six months, or at least about nine months.

The active compound can be first administered at any suitable time, e.g., within about 1 h, within about 2 h, within about 6 h, within about 12 h, or within about 18 h, within about 24 h, within about 2 days, or within about 1 week of radiation exposure.

Formulations

The active compound may be formulated into a pharmaceutical composition as is known in the art. Such compositions may include various components as are known in the art, e.g., see Remington: The Science and Practice of Pharmacy, (22nd ed.) ed. L. V. Allen, Jr., 2013, Pharmaceutical Press, Philadelphia, PA.

The composition may include a pharmaceutically acceptable carrier, e.g., any of those conventionally used and is limited only by chemico-physical considerations, such as solubility and lack of reactivity with the compound, and by the route of administration. The pharmaceutically acceptable carriers described herein, for example, vehicles, adjuvants, excipients, or diluents, are well known to those who are skilled in the art and are readily available to the public. It is preferred that the pharmaceutically acceptable carrier be one which is chemically inert to the active compounds and one which has no detrimental side effects or toxicity under the conditions of use.

Antioxidants

Pharmaceutical compositions employed in the methods may or may not include an antioxidant. The antioxidant may minimize the oxidative degradation of the active compound. Examples of antioxidants include, but are not limited to, 4-chloro-2,6-di-tert-butylphenol, tocopherol, alpha-tocopherol, alkylated diphenylamines, ascorbic acid, ascorbyl myristate, ascorbyl palmitate, ascorbyl stearate, beta-carotene, butylated hydroxyanisole, butylated hydroxytoluene, citric acid, cysteine, D-alpha-tocopheryl polyethylene glycol 1000 succinate, deferoxamine methanesulfonate, dodecyl gallate, ethylparaben, folic acid, fumaric acid, gallic acid, glutathione, lecithin, malic acid, methylparaben, monothioglycerol, N-acetyl cysteine, nordihydroguaiaretic acid, octyl gallate, p-phenylenediamine, potassium ascorbate, potassium metabisulfite, potassium sorbate, propionic acid, propyl gallate, retinol, sorbic acid, sodium ascorbate, sodium bisulfite, sodium hydrosulfite, sodium isoascorbate, sodium metabisulfite, sodium sulfite, sodium thiosulfate, tartaric acid, tert-butylhydroquinone, tocopheryl acetate, vitamin A, vitamin B6, vitamin B12, or vitamin E. In some embodiments, the methods of the invention may employ a pharmaceutical composition comprising ascorbic acid, tocopherol, retinol, ascorbyl palmitate, N-acetyl cysteine, glutathione, butylatedhydroxytoluene, and/or butylatedhydroxyanisole as antioxidant.

In some embodiments, the method includes a pharmaceutical composition that includes less than about 10% antioxidant by weight, e.g., less than about 9%, less than about 8%, less than about 7%, less than about 6%, less than about 5%, less than about 4%, less than about 3%, less than about 2%, or less than about 1%. In some embodiments, the method uses a pharmaceutical composition that includes about 2-9% antioxidant by total weight, e.g., about 2-4%, about 3-5%, about 4-6%, about 5-7%, about 6-8%, or about 7-9%. In some embodiments, the method uses a pharmaceutical composition that includes about 5-100% of the USP maximum daily dose of the antioxidant, e.g., in some embodiments, the method uses a pharmaceutical composition that includes about 5%, about 10%, about 15%, about 20%, about 30%, about 40%, about 50%, about 60%, about 70%, about 80%, about 90%, or about 100% of the USP maximum daily dose of the antioxidant. In some embodiments, the ratio of sepiapterin, tetrahydrobiopterin, or dihydrobiopterin, or pharmaceutically acceptable salt and/or co-crystal thereof, to antioxidant is at least about 1:1, e.g., at least about 2:1, at least about 3:1, at least about 4:1, at least about 5:1, at least about 6:1, at least about 7:1, at least about 8:1, at least about 9:1, or at least about 10:1 wt/wt. In some embodiments of the compositions described herein, the composition includes an antioxidant (e.g., ascorbic acid), wherein the ratio of the pharmaceutically acceptable salt and/or co-crystal of sepiapterin, tetrahydrobiopterin, or dihydrobiopterin to antioxidant is greater than about 4:1 (e.g., greater than about 5:1, greater than about 6:1, greater than about 7:1, greater than about 8:1, greater than about 9:1, greater than about 10:1, greater than about 15:1, or greater than about 20:1) by weight (e.g., the weight of the salt to antioxidant).

Dispersants

In some embodiments, the method uses a pharmaceutical composition that includes at least one dispersant. The dispersant may cause particles in the formulation to separate, e.g., release their medicinal substances on contact with moisture. Examples of dispersant include, but are not limited to, crosslinked polyvinylpyrrolidone, carboxymethylcellulose (e.g., croscarmellose salt, e.g., croscarmellose sodium), starch (e.g., sodium starch glycolate), or alginic acid. In some embodiments, the dispersant in the pharmaceutical composition is a carboxymethylcellulose such as a pharmaceutically acceptable salt of croscarmellose. In some embodiments, the method uses a pharmaceutical composition that may include about 0.1-1.5% dispersant by total weight, e.g., about 0.1%, about 0.5%, about 1%, or about 1.5%. In some embodiments, the method uses a pharmaceutical composition that includes less than about 1.5% dispersant, e.g., less than about 1%, less than about 0.5%, or less than about 0.1%.

Anti-Caking Agents

Anti-caking agents are often added to pharmaceutical compositions to prevent the formation of lumps, e.g., in solutions. Accordingly, in some embodiments, the pharmaceutical compositions used in the methods of the invention include at least one anti-caking agent. In some embodiments, the pharmaceutical compositions used in the methods of the invention include at least two anti-caking agents. Exemplary anti-caking agents include colloidal silicon dioxide, microcrystalline cellulose, tricalcium phosphate, microcrystalline cellulose, magnesium stearate, sodium bicarbonate, sodium ferrocyanide, potassium ferrocyanide, calcium ferrocyanide, calcium phosphate, sodium silicate, colloidal silicon dioxide, calcium silicate, magnesium trisilicate, talcum powder, sodium aluminosilicate, potassium aluminum silicate, calcium aluminosilicate, bentonite, aluminum silicate, stearic acid, and polydimethylsiloxane. In some embodiments, the at least one anti-caking agent is colloidal silicon dioxide or microcrystalline cellulose. In some embodiments, the pharmaceutical composition used in the methods of the invention may include about 65-75% anti-caking agent by total weight, e.g., about 65%, about 67%, about 70%, about 73%, or about 75%. In some embodiments, the pharmaceutical composition used in the methods of the invention includes both colloidal silicon dioxide and microcrystalline cellulose. In some embodiments, the pharmaceutical composition used in the methods of the invention includes about 60-65% microcrystalline cellulose by total weight and about 5-7% colloidal silicon dioxide by total weight.

Dosing Vehicle

In some embodiments, a pharmaceutical composition used in the methods of the invention is combined with a dosing vehicle prior to administration. In some embodiments, the composition may be administered in a dosing vehicle with a viscosity of approximately 50-1750 centipoise (cP), e.g., to aid suspension and dosing of the pharmaceutical composition. One type of suspending agent that can be used is a combination of glycerin and sucrose in water (e.g., MEDISCA® oral mix with 2.5% glycerin and 27% sucrose in water). An appropriate quantity of composition can be added to the dosing vehicle mixture and agitated to suspend the composition just prior to administration.

Other suspending agents may also be used as a dosing vehicle. Exemplary suspending agents include water, agar, alginic acid, sodium carboxymethyl cellulose, carrageenan, dextrin, gelatin, guar gum, hydroxyethyl cellulose, hydroxypropyl cellulose, hypromellose, methyl cellulose, polyethylene glycol, povidone, tragacanth, xanthan gum, or other suspending agents known in the art.

Routes of Administration

There is a wide variety of suitable formulations for use with the present invention. The following formulations for oral, aerosol, parenteral, subcutaneous, intravenous, intra-arterial, intramuscular, intraperitoneal, intrathecal, rectal, and vaginal administration are merely exemplary and are in no way limiting.

A pharmaceutical composition may be a liquid formulation, such as in the form of a solution, suspension, or emulsion. Formulations suitable for oral administration can consist of (a) capsules, sachets, tablets, lozenges, and troches, each containing a predetermined amount of the active ingredient, as solids or granules; (b) powders; (c) liquid solutions, such as an effective amount of the compound dissolved in diluents, such as water, saline, or orange juice; (d) suspensions in an appropriate liquid; and (e) suitable emulsions. Preferred are solid oral dosage forms such as capsule forms, tablet forms, and powder forms. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

Formulations suitable for oral and/or parenteral administration include aqueous and non-aqueous, isotonic sterile injection solutions, which can contain anti-oxidants, buffers, bacteriostats, and/or solutes that render the formulation isotonic with the blood of the intended recipient, and aqueous and non-aqueous sterile suspensions that can include suspending agents, solubilizers, thickening agents, stabilizers, and/or preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, benzyl alcohol, or hexadecyl alcohol, glycols, such as propylene glycol or polyethylene glycol and other polyethylene alcohols, glycerol ketals, such as 2,2-dimethyl-1,3-dioxolane-4-methanol, ethers, such as poly(ethylene glycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazopeak quaternary ammonium salts, and (3) mixtures thereof.

The parenteral formulations will typically contain from about 20 to about 30% by weight of active compound in solution. Suitable preservatives and buffers can be used in such formulations. In order to minimize or eliminate irritation at the site of injection, such compositions may contain one or more nonionic surfactants having a hydrophilic-lipophilic balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

A pharmaceutical composition may be an injectable formulation. The requirements for effective pharmaceutical carriers for injectable compositions are well known to those of ordinary skill in the art. See Remington: The Science and Practice of Pharmacy, (22nd ed.) ed. L. V. Allen, Jr., 2013, Pharmaceutical Press, Philadelphia, PA.

Topical formulations, including those that are useful for transdermal drug release, are well-known to those of skill in the art and are suitable in the context of the invention for application to skin. Topically applied compositions are generally in the form of liquids, creams, pastes, lotions and gels. Topical administration includes application to the oral mucosa, which includes the oral cavity, oral epithelium, palate, gingival, and the nasal mucosa. In some embodiments, the composition used in the methods of the present invention contains sepiapterin, tetrahydrobiopterin, or dihydrobiopterin, and a suitable vehicle or carrier. It may also contain other components, such as an anti-irritant. The carrier can be a liquid, solid or semi-solid. In some embodiments, the composition is an aqueous solution. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone-based materials.

A pharmaceutical composition may be an aerosol formulation to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Additionally, a pharmaceutical composition may be a suppository. Formulations suitable for vaginal administration may be presented as pessaries, tampons, creams, gels, pastes, foams, or spray formulas containing, in addition to the active ingredient, such carriers as are known in the art to be appropriate.

Solid Dosage Form for Oral Administration

Formulations for oral use include particles containing the active compound in a mixture with non-toxic pharmaceutically acceptable excipients, and such formulations are known to the skilled artisan (e.g., U.S. Pat. Nos. 5,817,307, 5,824,300, 5,830,456, 5,846,526, 5,882,640, 5,910,304, 6,036,949, 6,036,949, 6,372,218, hereby incorporated by reference). Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, anti-adhesives (e.g., magnesium stearate, zinc stearate, stearic acid, silicas, hydrogenated vegetable oils, or talc), and anti-caking agents (e.g., colloidal silicon dioxide, microcrystalline cellulose, tricalcium phosphate, microcrystalline cellulose, magnesium stearate, sodium bicarbonate, sodium ferrocyanide, potassium ferrocyanide, calcium ferrocyanide, calcium phosphate, sodium silicate, colloidal silicon dioxide, calcium silicate, magnesium trisilicate, talcum powder, sodium aluminosilicate, potassium aluminum silicate, calcium aluminosilicate, bentonite, aluminum silicate, stearic acid, polydimethylsiloxane). Other pharmaceutically acceptable excipients can be colorants, flavoring agents, plasticizers, humectants, and buffering agents. In some embodiments, excipients (e.g., flavoring agents) are packaged with the composition. In some embodiments, excipients (e.g., flavorings) are packaged separately from the composition (e.g., are combined with the composition prior to administration).

The solid compositions used in the methods of the invention may include a coating adapted to protect the composition from unwanted chemical changes, (e.g., chemical degradation prior to the release of the active substances). The coating may be applied on the solid dosage form in a similar manner as that described in Remington: The Science and Practice of Pharmacy, (22nd ed.) ed. L. V. Allen, Jr., 2013, Pharmaceutical Press, Philadelphia, PA.

Powders and granulates may be prepared using the ingredients mentioned above in a conventional manner using, e.g., a mixer, a fluid bed apparatus, melt congeal apparatus, rotor granulator, extrusion/spheronizer, or spray drying equipment.

EXAMPLES

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention. As such, the following examples are provided to teach various aspects of the present invention. These examples represent individual embodiments of the aspects of this invention and one skilled in the art will recognize that additional examples can be generated in order to equally teach the aspects of the present invention.

Example 1. Treatment of C57L/J Mice Groups

Animals

Both male and female C57L/J wild-type 6-8-week-old mice were purchased from Jackson Laboratory (Bar Harbor, ME). The mice were housed with a 12:12 h light-dark schedule and access to water and food ad libitum. The experiments were conducted under the guidelines of laboratory animals for biomedical research published by the National Institutes of Health (rev. 2011). The study protocol was approved by the Institutional Animal Care and Use Committee of Virginia Commonwealth University.

Experimental Treatment Plan

Equal numbers of male and female mice were distributed to each group. While under ketamine/xylazine anesthesia (100 mg/kg and 10 mg/kg, respectively) mice received 5 Gy total body irradiation (TBI), immediately followed by a top-up dose of 6.5 Gy to the thorax, for a total thoracic dose of 11.5 Gy, using a Varian 21 EX LINAC (Palo Alto, CA). Twenty-four hours post-irradiation, mice were treated once daily for 6 days by oral gavage with 1 mg/kg sepiapterin or 5 mg/kg BH4 dissolved in water (FIG. 1).

Example 2. Evaluation of Cardiac Function

Echocardiography

All mice underwent transthoracic echocardiography at baseline (before irradiation (IR)), at 8, 30, 60, 90 and 180 days, under light anesthesia (30 mg/kg pentobarbital sodium). Echocardiography was performed with the Vevo770 imaging system (VisualSonics, Toronto, Ontario, Canada) and a 30-MHz probe. The heart was visualized in B-mode from parasternal short-axis and apical views. The left ventricular (LV) end-diastolic diameter (EDD), LV end-systolic diameter (ESD), LV anterior wall diastolic thickness (AWDT), and LV posterior wall diastolic thickness (PWDT), LV anterior wall systolic thickness (AWST), and LV posterior wall systolic thickness (PWST) were measured at M-mode, according to the American Society of Echocardiography recommendations. LV ejection fraction (EF), and LV mass were calculated from the measurements of wall thickness and chamber diameters. The LVEF was derived using the Teicholz formula (LVEF=[LVEDD3−LVESD3]/LVEDD3), as previously described. The transmitral LV outflow tract Doppler spectra (E, A, ET) was recorded from an apical four-chamber view, and the myocardial performance index (MPI) was calculated as the ratio of isovolumetric contraction time (ICT) and isovolumetric relaxation time (IRT) divided by the ejection time (ED. The investigators performing and reading the echocardiograms were blinded to the treatment allocation. A beta-adrenergic agonist, isoproterenol (Sigma Aldrich, St. Louis, MO, USA) 20 ng/mouse, was used to assess cardiac contractility in irradiated mice without SP treatment. Cardiac contractility (contractile reserve) was expressed as percentage change in LVEF measured at rest (LVEFr) and 3 min after isoproterenol injection (LVEFi) and calculated as [(LVEFi−LVEFr)/LVEFr]*100. Measurements of the contractile reserve were taken at baseline, 8, 30, 60, 90 and 180 days after IR. Echocardiogram assessment was performed by an operator blinded to treatment allocation.

Effects of Sepia Pterin on IR-Induced Cardiomyopathy

Figure 2:
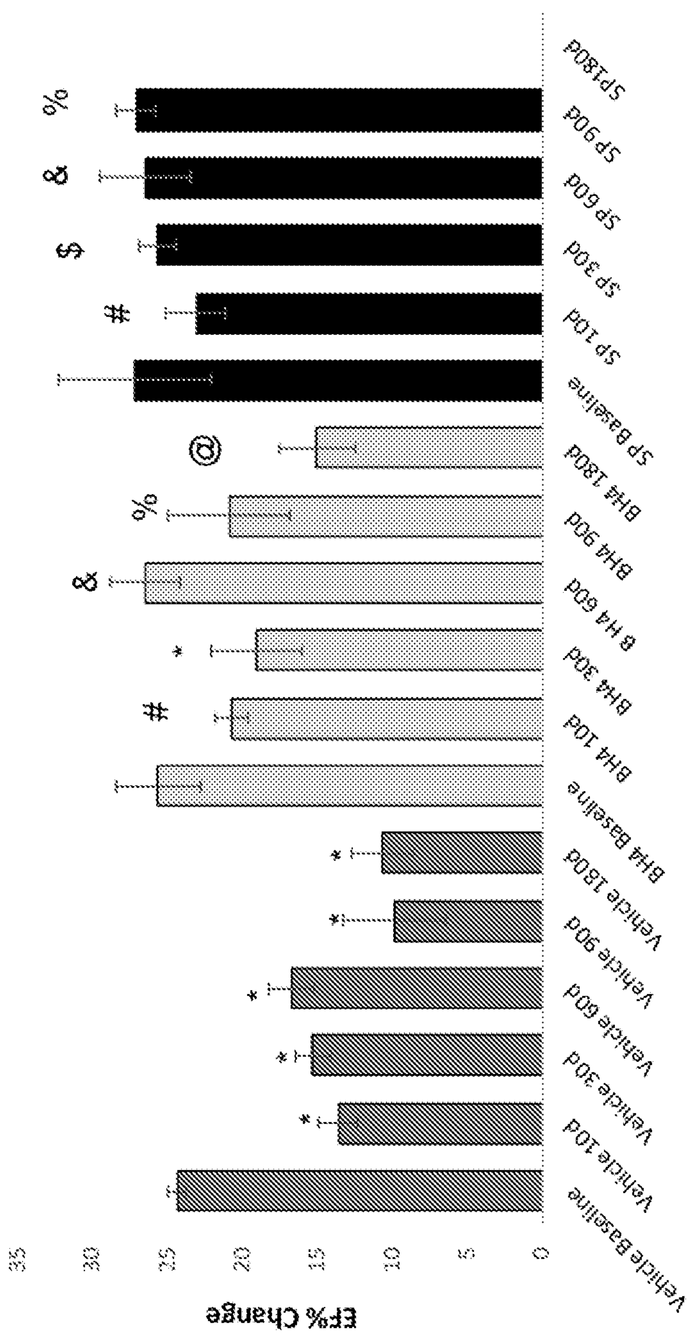
FIG. 2 illustrates the isoproterenol response in radiation-treated groups for vehicle-, BH4-, and SP-treated groups. Assessments of the contractile reserve were measured at 10, 30, 60, 90, and 180 days.
Figure 3:
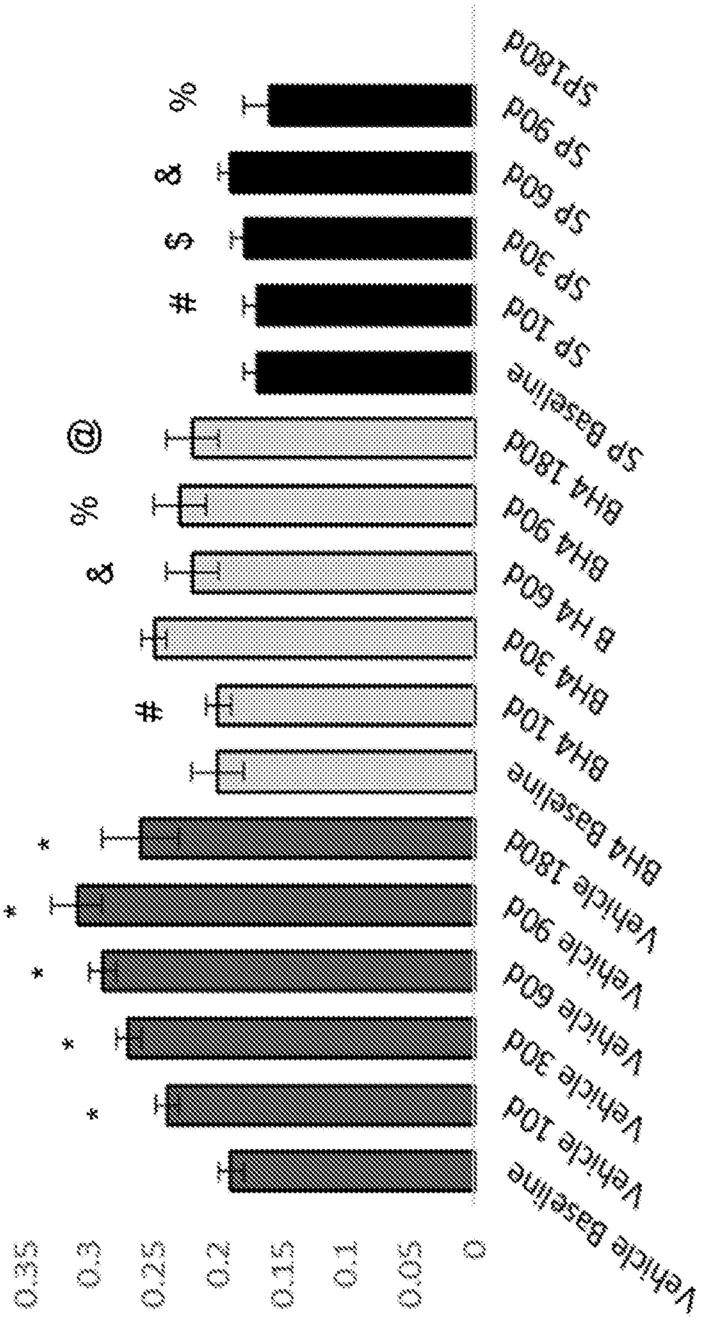
FIG. 3 illustrates the myocardial performance index of radiation-treated groups for vehicle-, BH4-, and SP-treated groups. Assessments of the myocardial performance index were measured at 10, 30, 60, 90, and 180 days.
Figure 7:
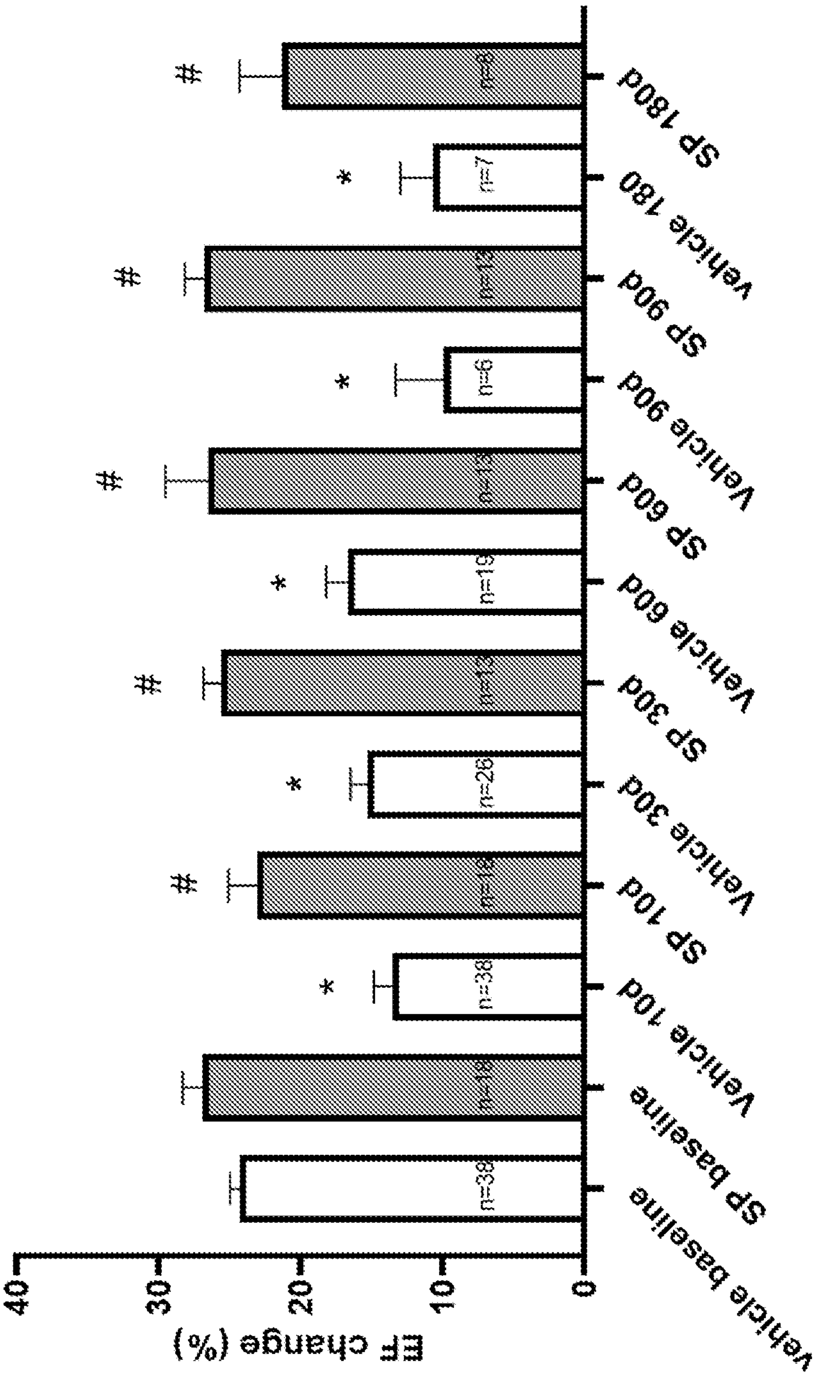
FIG. 7 illustrates the isoproterenol response in radiation-treated groups for vehicle- or SP-treated groups. Assessment of the contractile reserve were measured at 0, 30, 60, 90, and 180 days. Radiation induces a reduction in contractile reserve in the irradiated vehicle-group compare to the vehicle baseline (*$p<0.05$ vs baseline) at 10, 30, 60, 90 and 180 days after irradiation. Administration of SP for 6 days blunted the drop in the contractile reserve at all the time points (#$p<0.05$ vs. vehicle same time point). Data represented as mean±SEM.
Figure 8:
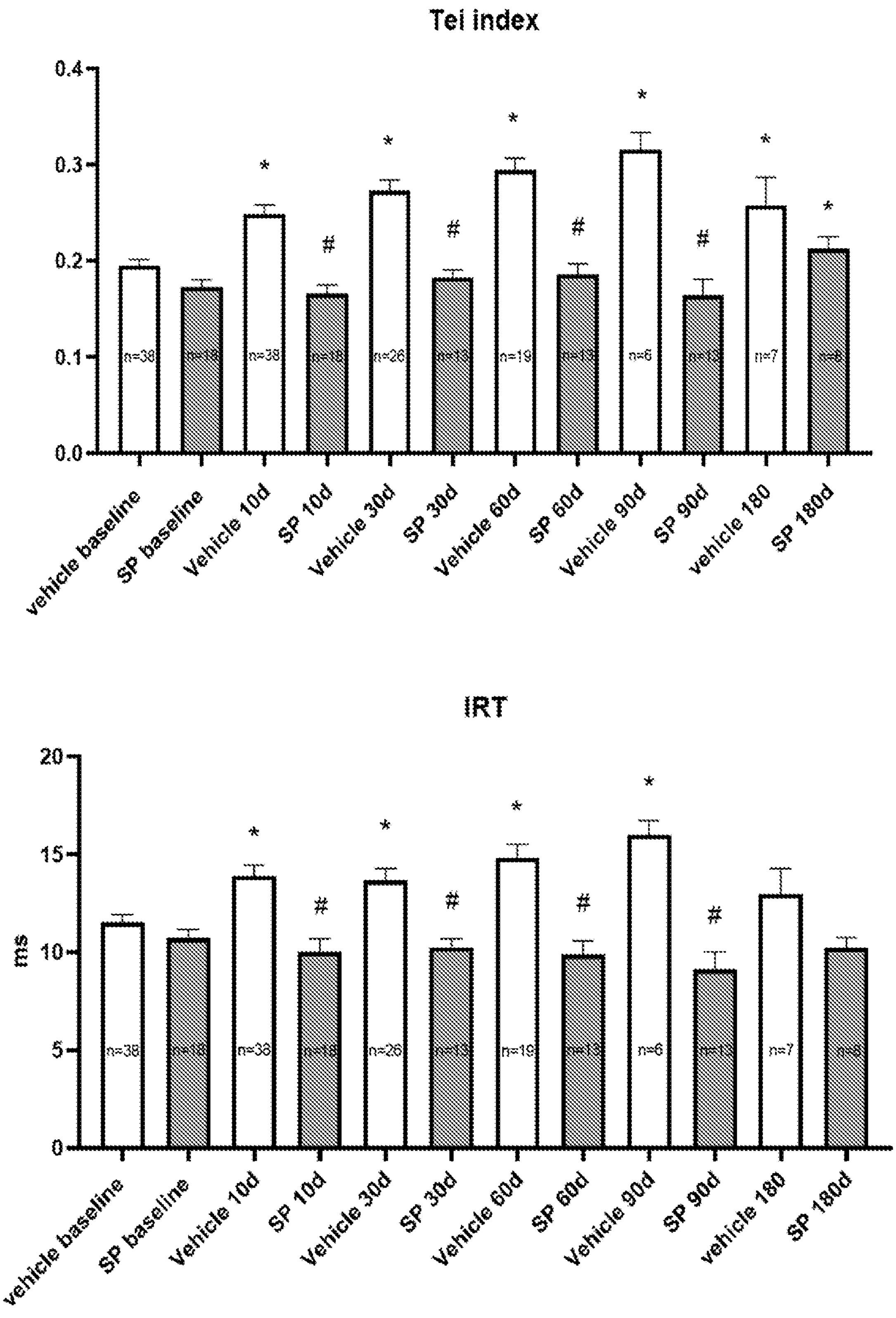
FIG. 8 illustrates the systolic and diastolic functions of vehicle- or SP-treated groups 10, 30, 60, 90, and 180 days after radiation treatment. The data are plotted as the Tei index and isovolumic relaxation time (IRT). Radiation induced inhibition of systolic (Tei index) and diastolic (Tei index and IRT) functions are mitigated by sepiapterin. Irradiated mice treated with vehicle showed a significant progressive increase (*$P<0.05$ vs. baseline) in the Tei and IRT starting at 10 days and up to 180 days. Administration of SP for 6 days blunted the increase in the Tei index and IRT at all the time points (#$p<0.05$ vs. vehicle same time point). Data represented as mean±SEM.
Figure 16A:
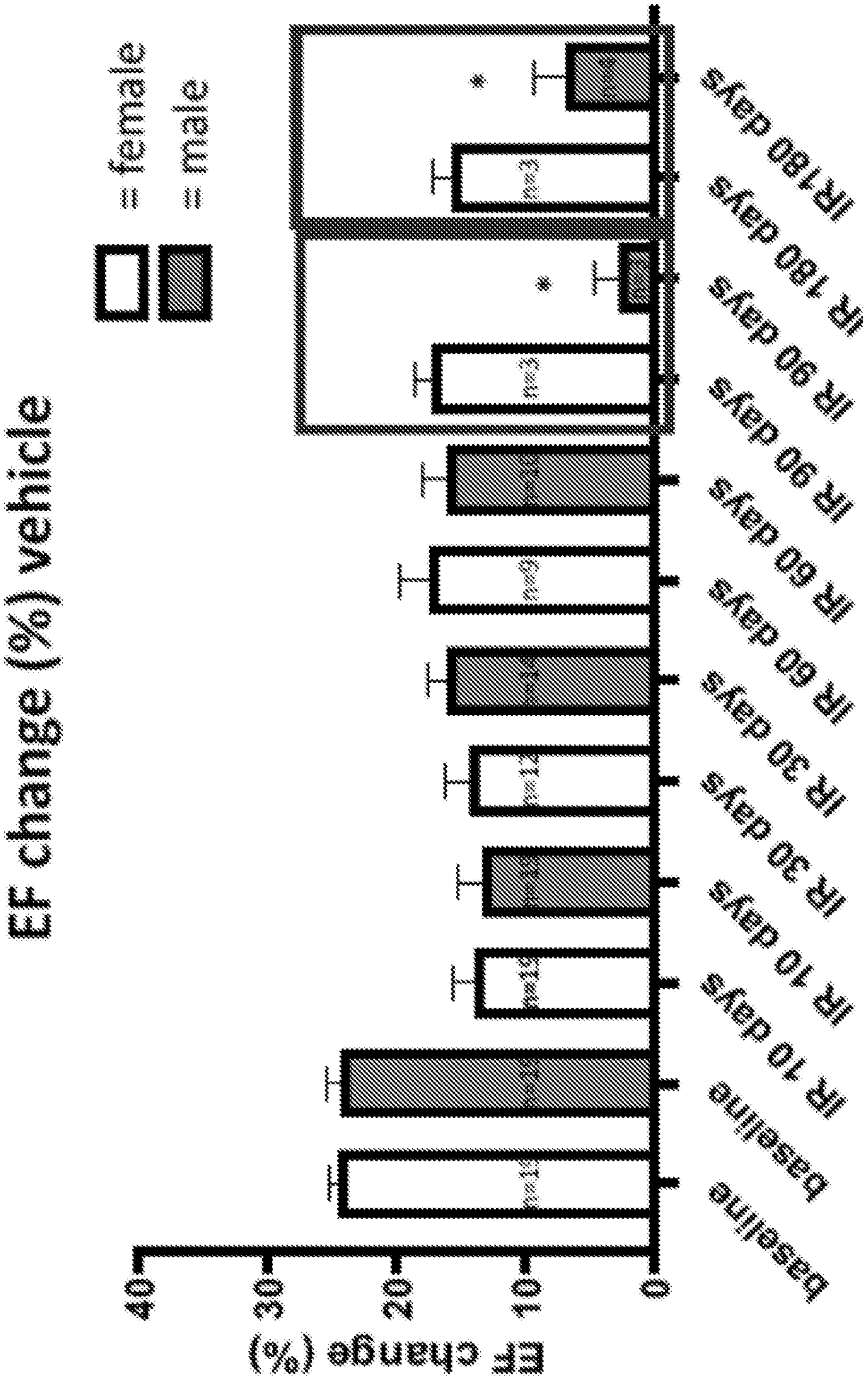
FIGS. 16A-16B illustrate the effect of vehicle (16A) and SP (16B) on the contractile reserve evaluated by sex.
Figure 16B:
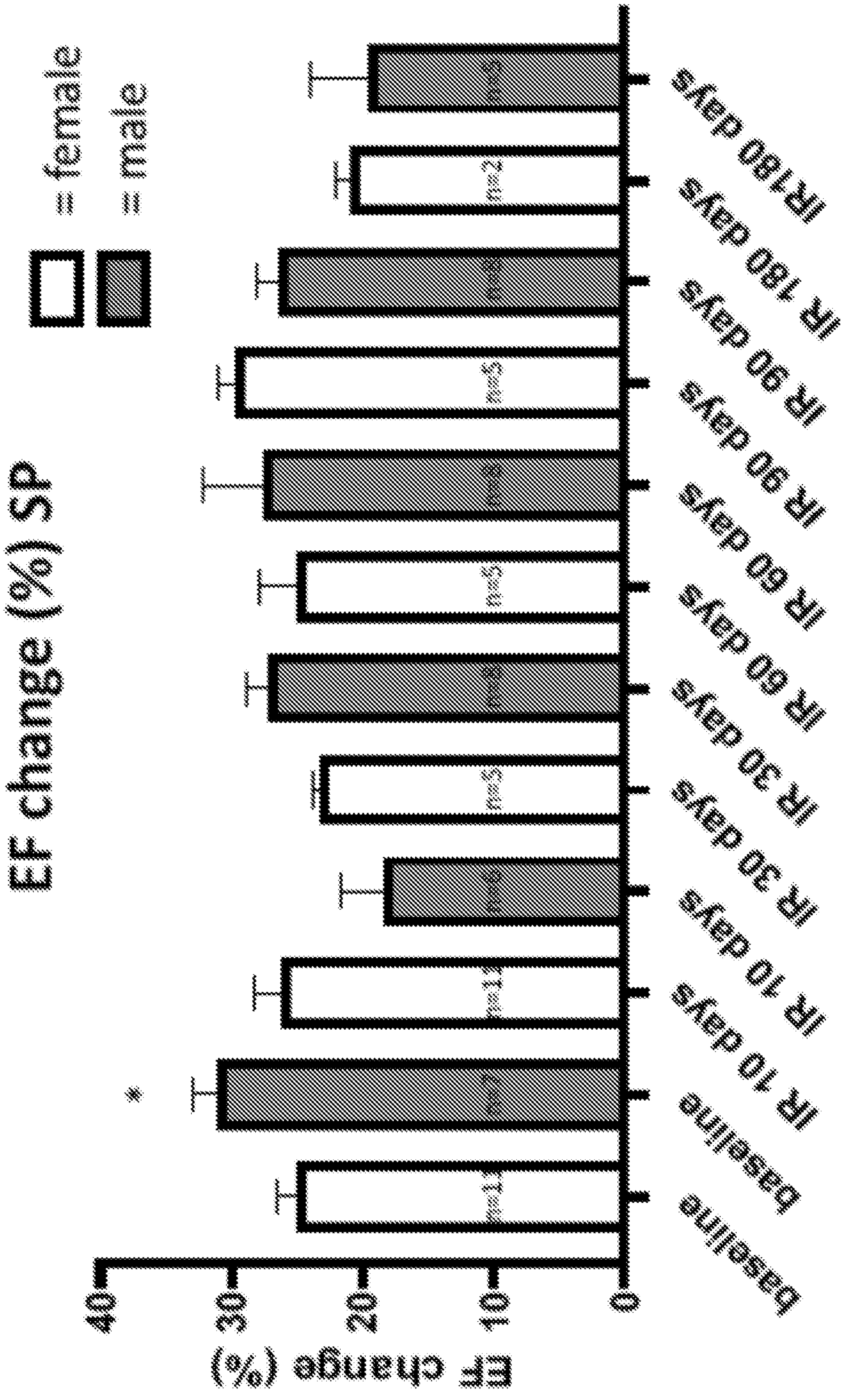

Cardiac performance was assessed at baseline in all mice before receiving IR and before starting SP treatment. The mice were then randomly assigned to the treatment groups (vehicle or SP) after receiving IR. The impact of our TBI model was evaluated with a thoracic top-up dose on the systolic and diastolic function as well as the contractile reserve in response to isoproterenol. Radiation induced a blunted response to isoproterenol (FIGS. 2 and 7) as well an increase in myocardial performance index (FIGS. 3 and 8) and isovolumetric relaxation time. Daily oral SP administration for 6 days after IR was able to restore the response to beta-adrenergic stimulation by isoproterenol. Furthermore SP treatment reduced the progression of the systolic and diastolic dysfunction, ameliorating the progressive increase in myocardial performance index and IRT. These results were further evaluated according to sex of the animal. In terms of systolic and diastolic function there were no significant differences in heart function response to radiation or 1 mg/kg SP (FIGS. 14A-14B and 15A-15B). However, in males there was additional significant loss in contractile reserve at 90 and 180 days post-IR compared to female mice (FIGS. 16A-16B). Importantly with both sexes, SP was equally effective in mitigating this loss in contractile reserve.

Example 3. Evaluation of Pulmonary Function

Assessment of Lung Injury by Breathing Rate

The breathing rate was measured every other week starting in week 6 using the Mouse Ox system (STARR Life Sciences Corp., Allison Park, PA). The animal was placed under ketamine/xylazine anesthesia and shaved in the area of analysis. 10 min post injection the animal was placed in a supine position with the sensor clipped to the upper thigh. The breathing rate was recorded for 3 min. The breathing rate was calculated using an algorithm in the Mouse Ox software.

SP and BH4 Reduce Radiation-Induced Loss of Pulmonary Function

Figure 5:
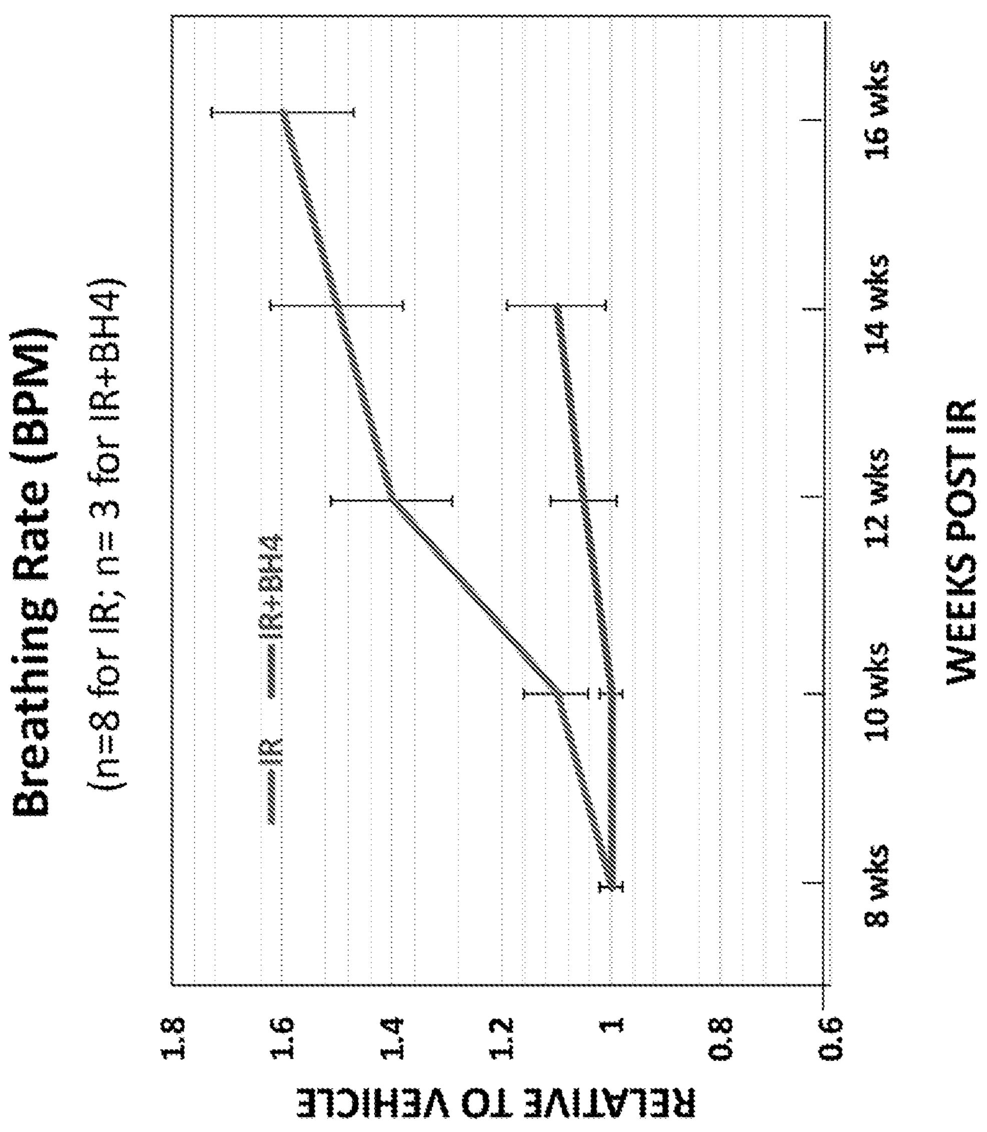
FIG. 5 illustrates the breathing rate of the radiation-treated experimental groups relative to the control groups.
Figure 9:
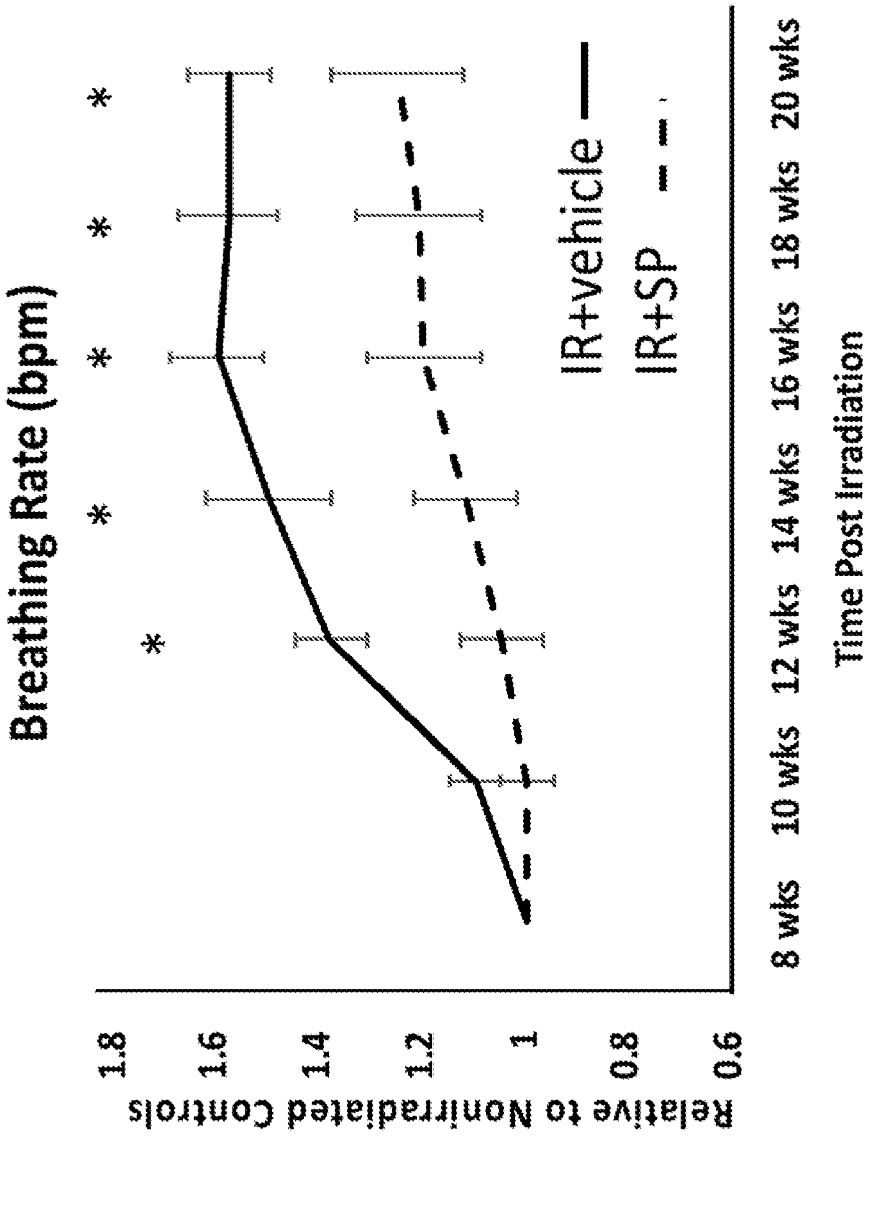
FIG. 9 illustrates lung function for radiation-treated experimental groups treated with vehicle or SP. The breathing rate was recorded for 5 min every 2 weeks. SP-treated mice had significantly improved pulmonary function at all points measured. n=7-12 for irradiated+vehicle, and n=8-14 for irradiated+SP. *p<0.05

Using the MouseOx system the breathing rate was measured in mice as a measure of respiratory function in the irradiated, the irradiated with SP (FIG. 9), and the irradiated with BH4 (FIG. 5) mice. The mice receiving 1 mg/kg/day SP or 5 mg/kg BH4 for 6 days had a significant delay in the development of lung injury, 14 weeks with SP and 10 weeks with vehicle, and a significantly reduced impairment of lung function at all points measured compared to vehicle treated mice.

Example 4. Survival Assessment of Mice Groups

SP Improves Survival Post Radiation

Figure 4:
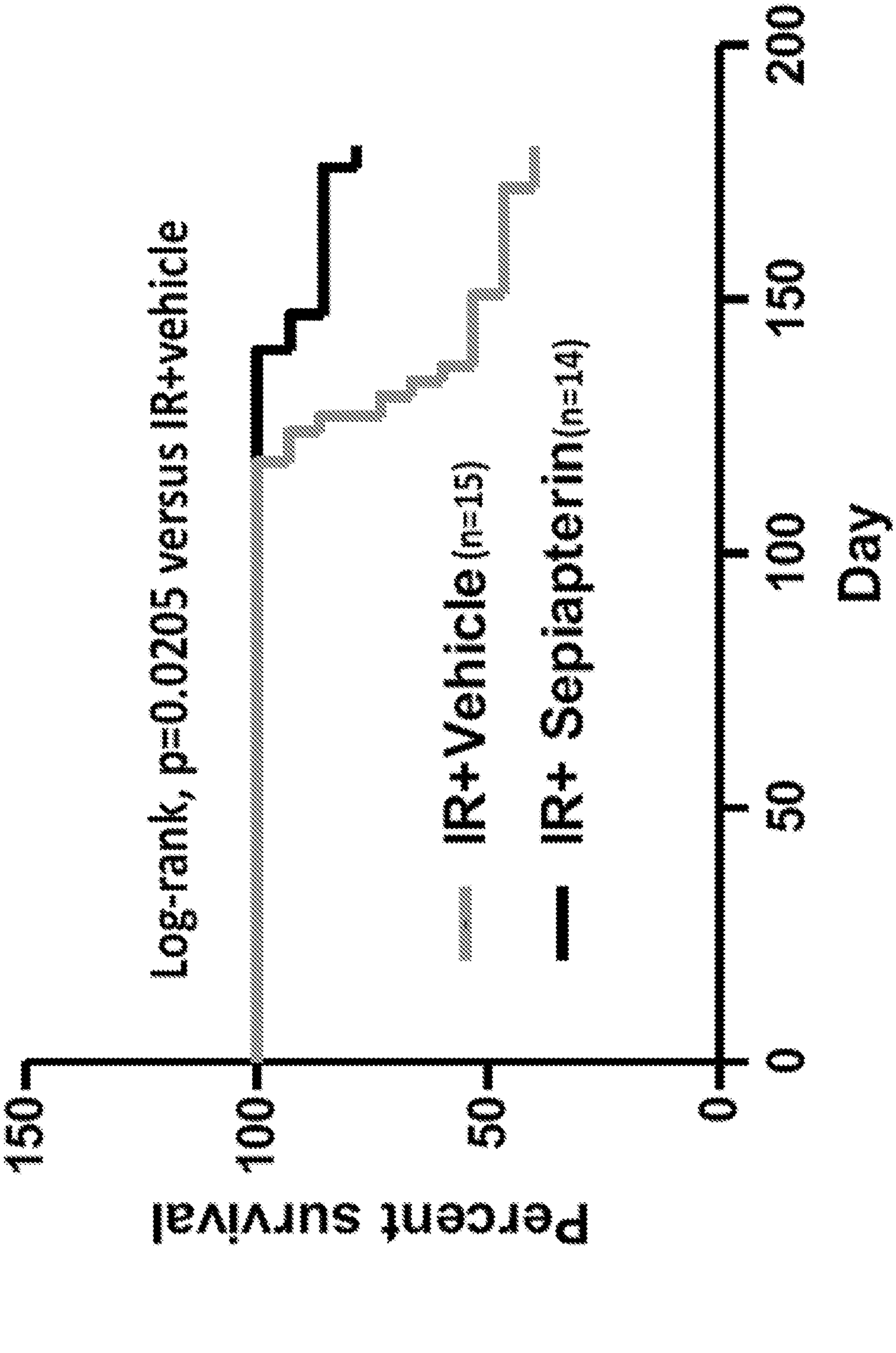
FIG. 4 illustrates the survival rate of experimental groups treated with radiation followed by vehicle or SP.

To determine whether the improved cardiopulmonary function impacted overall survival the mice were followed over 180 days post IR. FIG. 4 shows the Kaplan Meyer survival plot for C57L/J mice following a total 11.5 Gy dose to the thorax (5 Gy TBI followed with 6.5 Gy dose to the thoracic) with and without 1 mg/kg/day SP for 6 days. Mice exposed to radiation without treatment resulted in a significant reduction in survival with a median survival of 137 days and 40% survival at the end of the study. In contrast, mice treated with 1 mg/kg/day SP for 6 days had significantly delayed and overall improved survival with 71% of the mice alive at 180 days, the end of the study.

Example 5. Serum Exosomal miRNA Expression

Figure 6A:
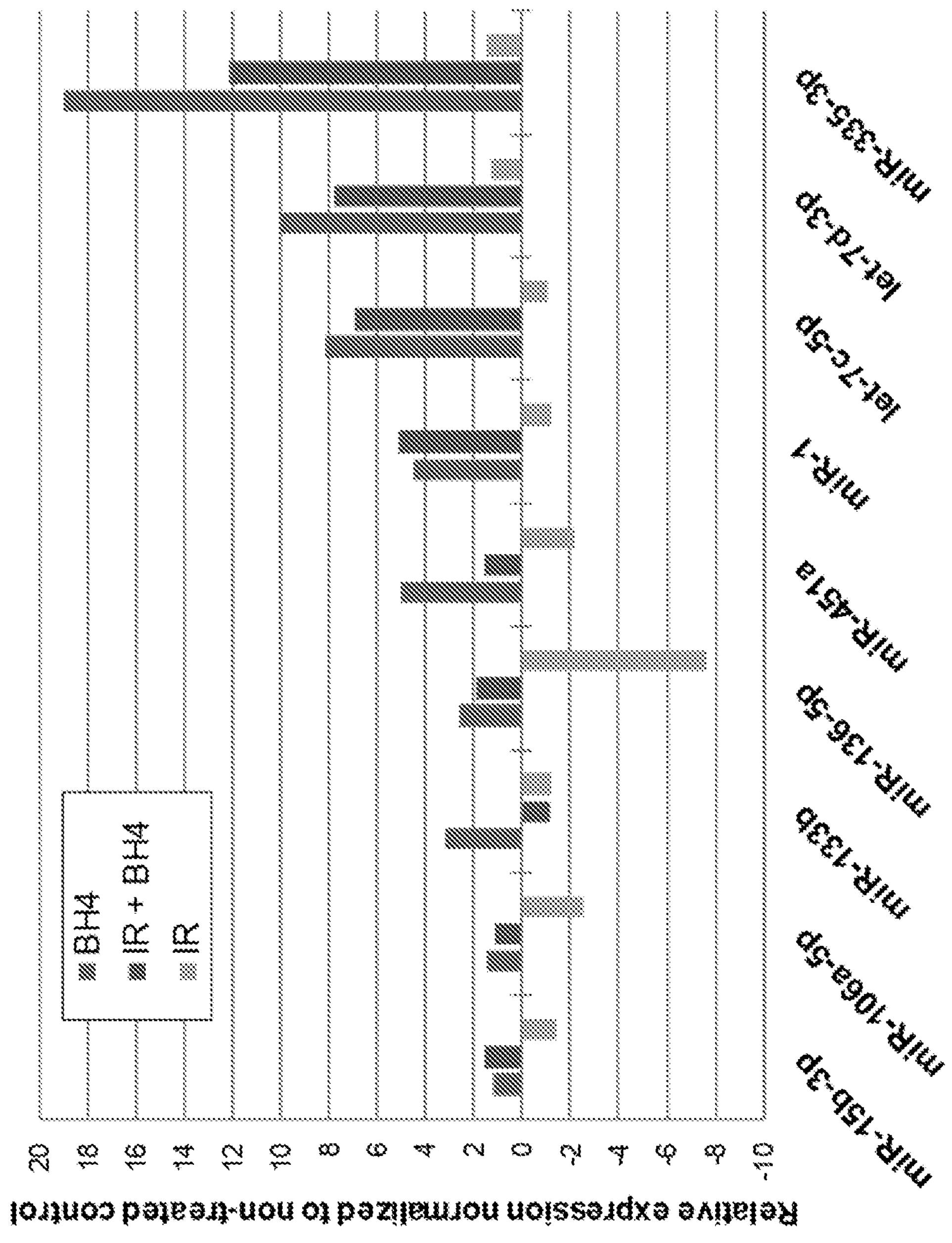
FIGS. 6A-6C illustrate the relative expression of serum exosomal miRNAs after radiation treatment, normalized to the non-treated control group. Data are provided on experimental groups treated with radiation, BH4, or both (6A) and radiation, sepiapterin, or both (6B (inhibited expression) and 6C (induced expression)).

Blood was collected by cardiac puncture using EDTA vials. Blood samples were centrifuged 3,000×g for 25 minutes, and plasma fraction was aliquoted and saved in a vapor phase of liquid nitrogen. Exosomes were isolated from the plasma of mice at the time points shown in FIGS. 6A-6C using an Exosome isolation kit from 101Bio. Exosome concentrations were quantified by EXOCET Exosome Quantitation Kit (System Biosciences). Equal exosome number from 5 animals were combined for each time point, and total exosomal RNA was extracted by using miRNeasy Micro Kit (QIAGEN). For the miRNAs expression profiling the miRCURY LNA™ Universal RT microRNA PCR assay (QIAGEN) and ExiLENT SYBR® Green Maser Mix (QIAGEN) were used. The initial estimation of exosomal miRNAs expression was performed by using Serum/Plasma LNA™ miRNA PCR Panel (Cat. #YAHS-106Y. QIAGEN) on the QuantStudio 5 RT-PCR machine (Applied Biosystems).

Figure 6B:
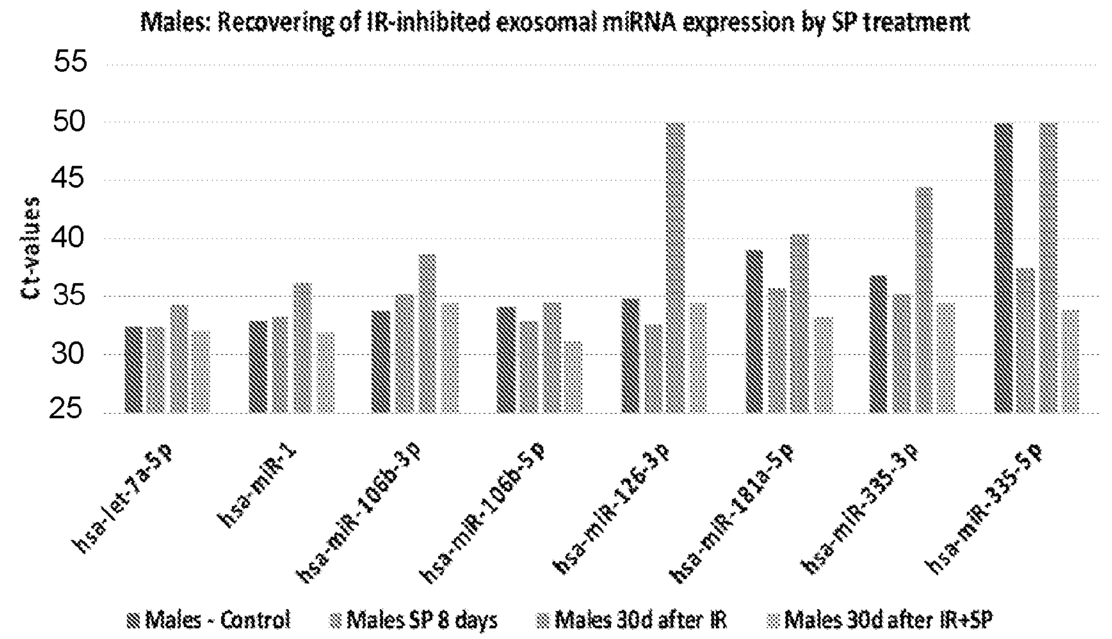
Figure 6B:
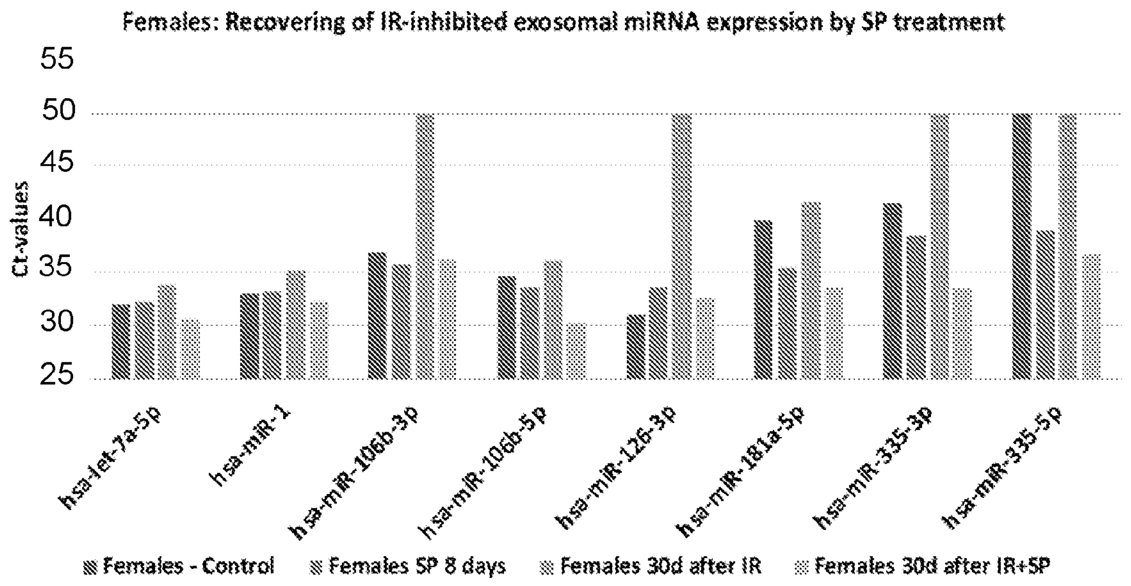
Figure 6C:
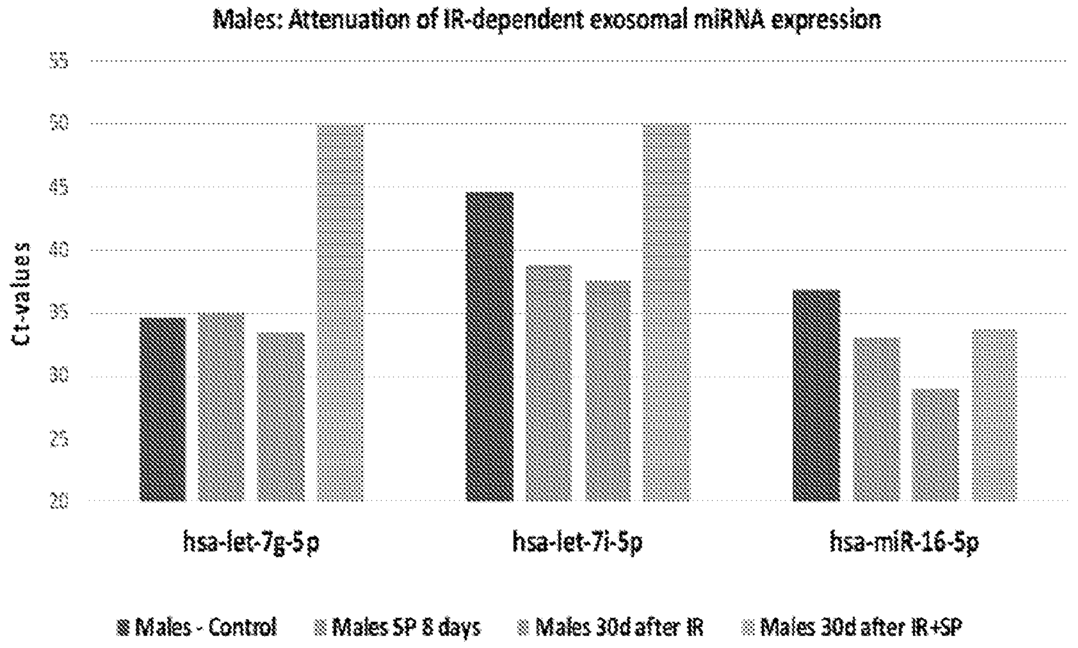
Figure 6C:
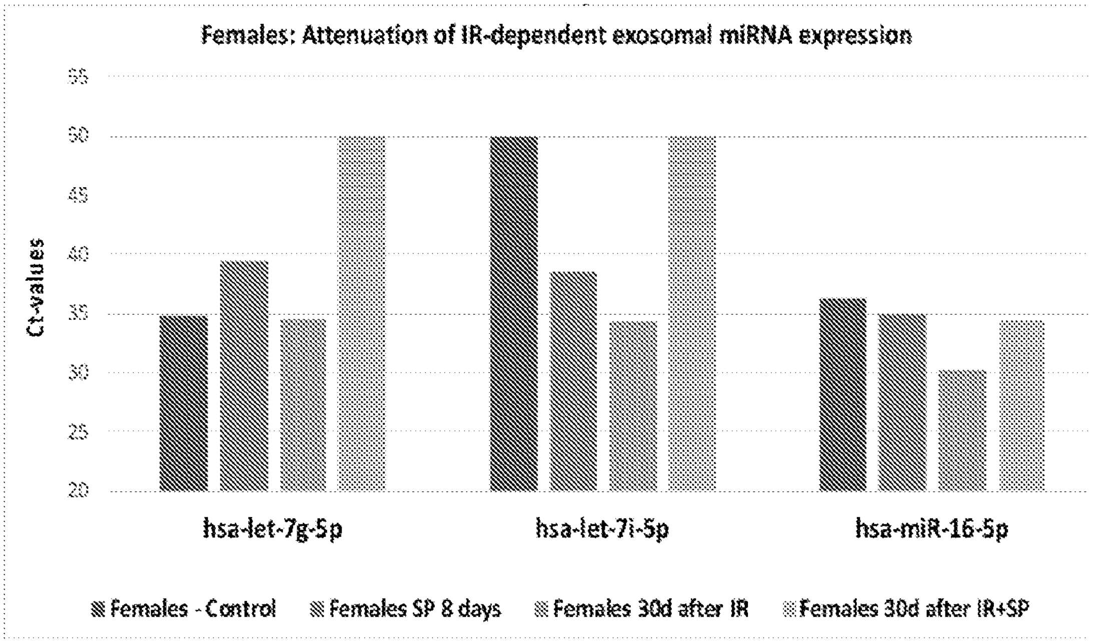

The cycle threshold values (Ct-values) shown in FIGS. 6B-6C are averages from 5 mice per group and are normalized to hsa-miR-145-5p and hsa-miR-221-3p experimentally demonstrated to be high quality normalization controls. Two different groups of exosomal miRNA demonstrating significant difference between vehicle-treated and SP-treated animals on 30 days time-point after IR were revealed. The first group included let-7a-5p, miR-1, miR-106b-3p, miR-106b-5p, miR-126-3p, miR-181a-5p, miR-335-3p, and miR-335-5p. Expression of miRNAs in this group was significantly lower in vehicle-treated animals comparing with SP-treated animals. In the second group expression of miRNAs was significantly higher in vehicle-treated animals comparing with SP-treated animals. The second group included let-7g-5p, let-7i-5p, and miR-16-5p. There were no significant differences between males and females both in terms of exosomal miRNA expression altered by IR or the effects of sepiapterin on miRNA expression. The miRNAs that demonstrated significant changes in expression due to radiation and were modulated by sepiapterin are involved in inflammatory processes (e.g. let-7a-5p, miR-106b-3p, miR-181a-5p, let-7i-5p), angiogenesis and vascular integrity (miR-106b-3p, miR-126-3p), cardiac inflammation and fibrosis (miR-335-5p, let-7i-5p, miR-126-3p, miR-16-5p). miR-16-5p inhibits TGF-beta/VEGF signaling. Treatment with BH4 (FIG. 6A) showed increases in expression of miR-15b-3p, miR-106a-5p, miR-133b, miR-136-5p, miR-451a, miR-1, miR-335-3p, let-7d-3p, and/or let-7c-5p.

Example 6. Cytokine mRNA Expression in Heart and Lung Tissue

RNA isolation and RT-PCR

Total RNA was isolated from the lung and heart tissue samples following the manufacturers instructions with the RNeasy Mini kit (Qiagen). The RNA concentration was evaluated by using a NanoDrop ND-1000 spectrophotometer (Thermo Scientific). RNA purity was assessed by the ratios of A260/A280 and A260/A230. RNA integrity was evaluated by the ratio of 28S/18S ribosomal RNA (rRNA) and the RNA integrity number (RIN) using an Agilent 2100 BioAnalyzer (Agilent Technologies). cDNA synthesis and genomic DNA elimination were performed by using RT2 First Strand Kit (QIAGEN). Samples were amplified using RT2 SYBR® Green qPCR Mastermix probes from QIAGEN on the QuantStudio 5 RT-PCR machine (Applied Biosystems). The following RT2 qPCR Primer Assays (QIAGEN) were used: Mouse Actin-β (NM_007393), Mouse Bmp2 (NM_007553), Mouse Ccl2 (NM_011333), Mouse Ctgf (NM_010217), Mouse IL-1β (NM_008361), Mouse IL-6 (NM_031168), Mouse IL-10 (NM_010548), Mouse IL-17α (NM_010552), Mouse Runx2 (NM_001145920), Mouse Spp1 (NM_001204201), Mouse TGF-β1 (NM_011577), Mouse Trim72 (NM_001079932).

Changes in mRNA Expression of Cytokines after Radiation

Figure 10:
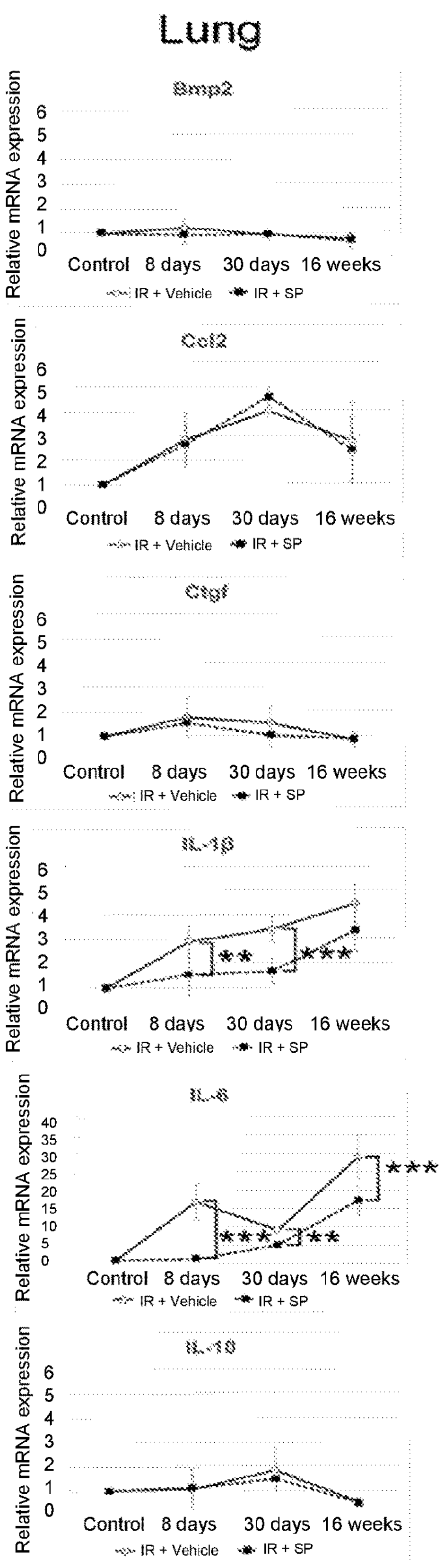
FIG. 10 illustrates the changes in mRNA expression of cytokines in heart and lung tissue. The data plotted represent the radiation-treated experimental groups treated with vehicle or SP. Post-irradiation changes of cytokines' mRNA expression in lung and heart tissue of animals treated with vehicle or SP. Lung and heart tissues were collected from animals at the different times post-irradiation. Total RNA was extracted from all tissue samples, and qPCR was performed for cytokines' mRNAs. Data are presented as the mean±SD for 5-6 animals in each group. The P-value was calculated with the Student t-test and shown as: —p<0.05; *—p<0.001.
Figure 10:
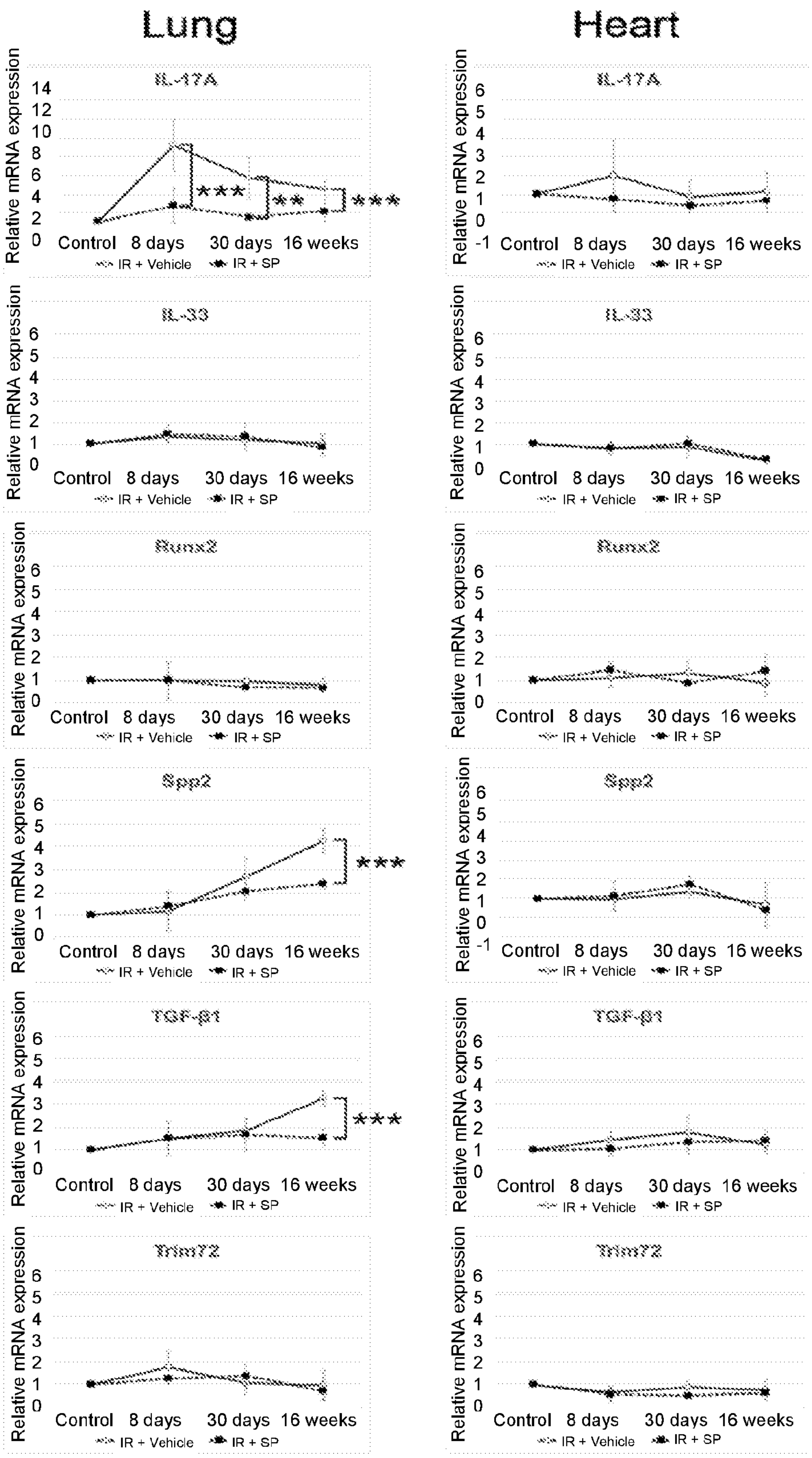

The expression of different cytokines (Bmp2, Ccl2, Ctgf, IL-1β, IL-6, IL-10, IL-17A, IL-33, Runx2, Spp2, TGF-β1, and Trim72) in lung and heart tissues were evaluated after radiation of animals and treatment 24 hrs later with 6 days of SP or water. mRNAs expression in tissue samples were tested in three different time-points after IR (8 days, 30 days, 16 weeks) and compared mRNAs expression in non-treated non-irradiated control animals (FIG. 10). All evaluated cytokines showed no significant difference in expression between Vehicle-treated and SP-treated groups of animals in heart tissue. In the lung tissue cytokines IL-1β, IL-6, IL-17A, Spp2, and TGF-β1 demonstrated significant difference in expression between Vehicle-treated and SP-treated groups of animals in the different time-points after IR. Vehicle-treated group of animals demonstrated significantly higher relative expression of IL-1β in lung tissue comparing with SP-treated group on 8 days and 30 days time-points (2.9±0.649 vs 1.54±0.825 and 3.39±0.532 vs 1.66±0.51 respectively). Relative expression of IL-6 was significantly higher in Vehicle-treated group comparing with SP-treated group in all time-points after IR (8 days: 16.88±4.91 vs 1.36±0.509; 30 days: 9.09±0.533 vs 4.96±0.905; 16 weeks: 28.85±5.987 vs 17.05±4.12). Along with the IL-6, cytokine IL-17A also demonstrated significantly higher expression in Vehicle-treated group comparing with SP-treated group in all time-points after IR (8 days: 9.19±2.783 vs 2.71±1.874; 30 days: 5.65±2.263 vs 1.49±0.379; 16 weeks: 4.5±0.824 vs 2.12±1.173). Cytokines Spp2 and TGF-β1 demonstrated significantly higher lung tissue expression in Vehicle-treated group comparing with SP-treated group on 16 weeks after IR (4.25±0.537 vs 2.38±0.211 and 3.26±0.339 vs 1.53±0.367). Cytokine Ccl2 demonstrated significant increase in relative expression in lung tissue on 30 days time-point for all animals with no significant difference between Vehicle-treated and SP-treated animal groups.

Example 7. IHC Analysis of Heart and Lung Tissue

IHC Analysis

Figure 11A:
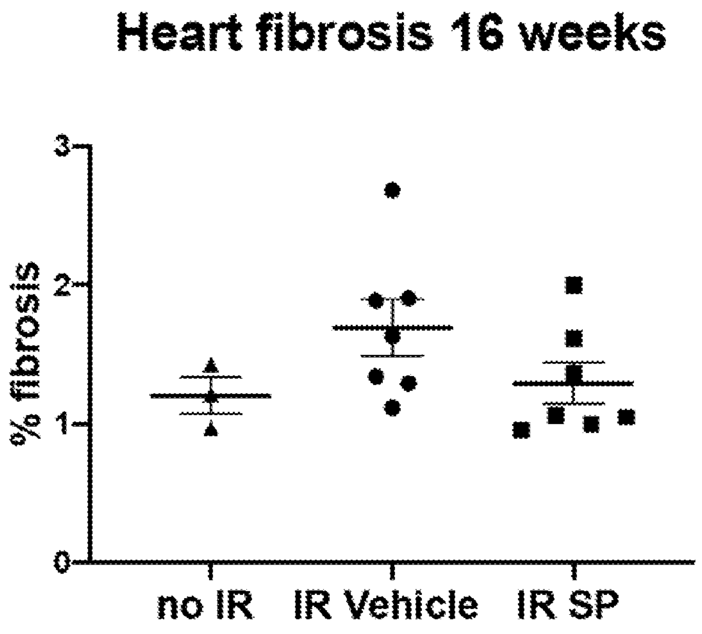
FIGS. 11A-11C illustrate the immunohistochemical (IHC) (11A-11B) and hydroxyproline (11C) analyses of control groups alongside radiation-treated experimental groups treated with vehicle or SP measured at 16 weeks.
Figure 11B:
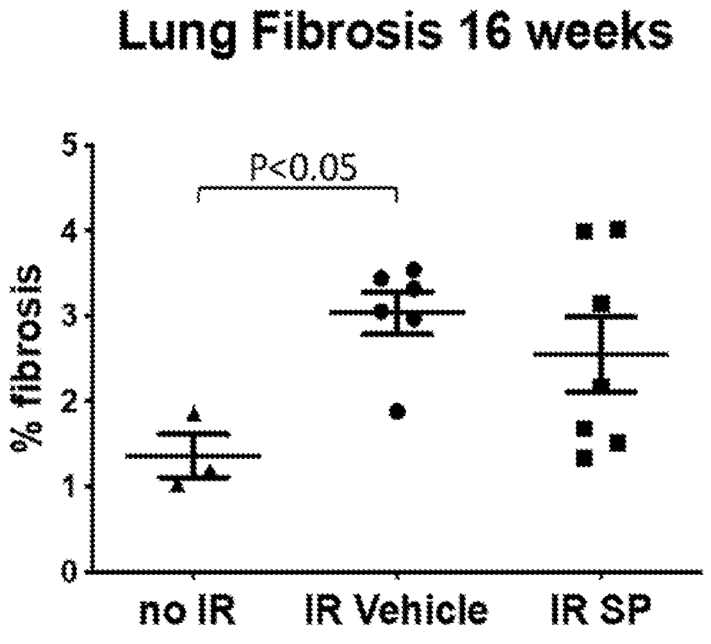
Figure 11C:
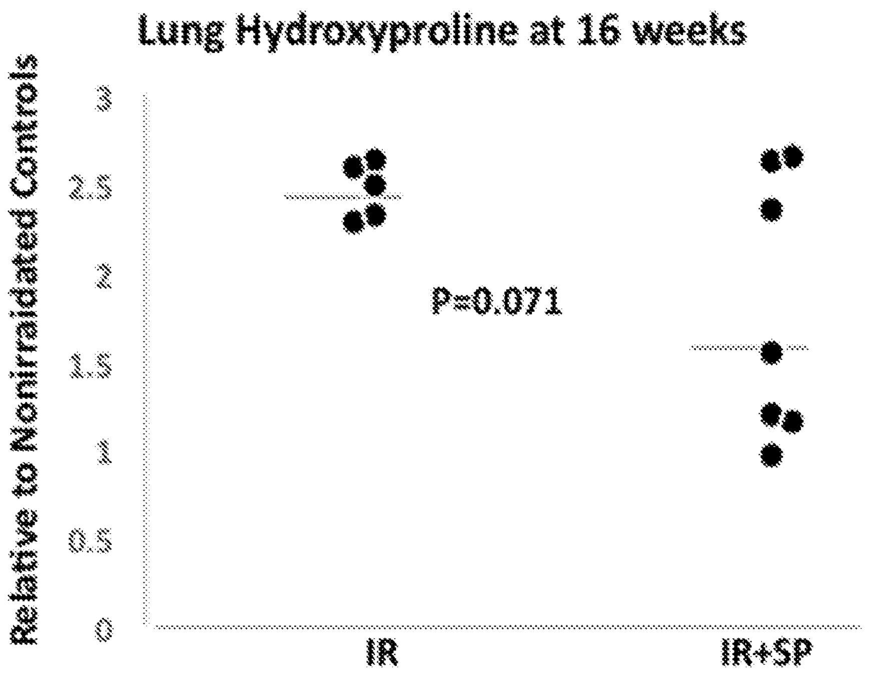

Sixteen weeks after IR, the hearts and the right lungs were collected for histological analysis (FIGS. 11A-11C). Hearts were collected in formalin, embedded in paraffin, and sliced in 5-mm sections. Right lungs were perfused with OCT and sliced in 6-mm sections. Masson's trichrome staining was performed to detect collagen fibers following the supplier's instructions (Richard-Allan Scientific Masson's trichrome kit, Thermo Fisher Scientific, Waltham, MA, USA). The area of myocardial and lung fibrosis was calculated as percentage of collagen area on total tissue area using computer morphometric analysis (Image ProPlus 6.0 software, Media Cybernetics, Rockville, MD, USA). Inflammation, angiogenesis and smooth muscle cells differentiation were measured staining the hearts and right lungs with the following antibodies: Ly-6G/Ly-6C (Invitrogen, Carlsbad, CA, USA), F40180 and alpha-sma (Cell Signaling, Danvers. MA, USA), CD-31 (BD Pharmigen, San Jose, CA, USA). Primary antibodies were detected by secondary antibodies followed by stained with Novared (Vector Laboratories, Burlingame, CA, USA) for antibodies detection. The assessment of the staining was done by two investigators blinded to treatment allocation on a dicothomic (positive/negative) basis and positive results were subsequently graded as mild (1), moderate (2) or intense (3) staining depending on the intensity and the extension of the staining.

Hydroxyproline

Hydroxyproline content was measured in the left upper lobe of the lung using the hydroxyproline assay kit from Sigma Aldrich (St. Louis, MO) as previously described.

Example 8. ELISA-Measured Proteins

Plasma Analyses

At the time of sacrifice, blood was obtained by heart puncture into EDTA containing tubes and centrifuged at 3000 rpm for 25 mins to isolate the plasma. The following ELISA plates from Abcam were used for analysis: fibrinogen (ab213478), neutrophil elastase (ab252356), C-reactive protein (ab157712) and IL-6 (ab100713). Plasma samples were processed and ELISA kits were run according to manufacturer recommendations. All cytokines were reported with an absolute unit. Key molecular players of the coagulation cascade like tissue factor, thrombin, and fibrinogen are epidemiologically and mechanistically linked with an inflammatory component. Genetic and pharmacologic studies have unraveled pivotal roles for fibrinogen in determining the extent of local or systemic inflammation. Neutrophil elastase, a serine protease present in the azurophil granules of neutrophils, is released in an inflammatory state and disintegrates extracellular matrices due to its low substrate specificity, resulting in tissue injury. Neutrophil elastase is one of the most destructive enzymes in the body. Once unregulated, this enzyme disturbs the function of the lung permeability barrier and induces the release of pro-inflammatory cytokines with stimulation of acute lung injury. An inflammatory cytokine IL-6 can be up-regulated as early as 6 hrs after radiation in lung tissue and blood. High levels of IL-6 in blood plasma may exacerbate the inflammatory response in the lung tissue, which ultimately causes IL-6 leakage to bronchoalveolae and further lung damage. High levels of IL-6 in the lung tissue may attract more inflammatory cells such as neutrophils, monocytes, macrophages to the injured local lung which ultimately causes serious damage to the lung and leads to chronic fibrosis. An acute raise of IL-6 in plasma can lead to increases in C Reactive Protein (CRP). C Reactive Protein (CRP) is produced by the liver and is a biomarker for general stress response to inflammation or infectious agents. It was shown that serum CRP level may be an effective indicator for predicting the occurrence of radiation pneumonitis and valuable factor for evaluating radiation-induced lung-injury extent.

Changes in Concentration of Cytokines in Plasma after IR

Figure 13A:
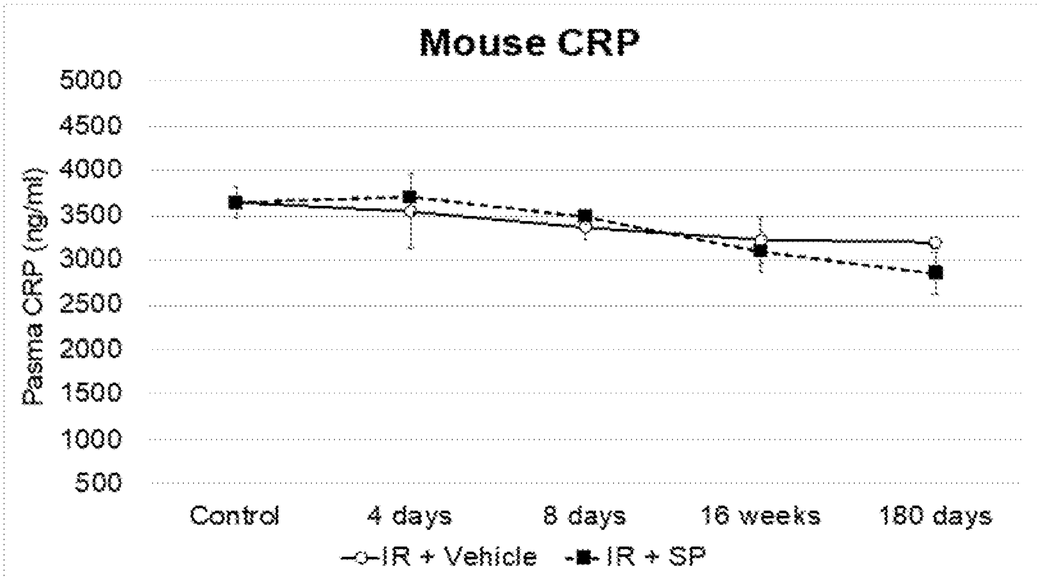
FIGS. 13A-13D illustrate ELISA measured proteins that are potential biomarkers: CRP (13A), fibrinogen (13B), IL-6 (13C), and neutrophil elastase (13D). Measurements of radiation-treated experimental groups treated with vehicle or SP were taken at 4 days, 8 days, 16 weeks, and 180 days and were compared to the control group.
Figure 13B:
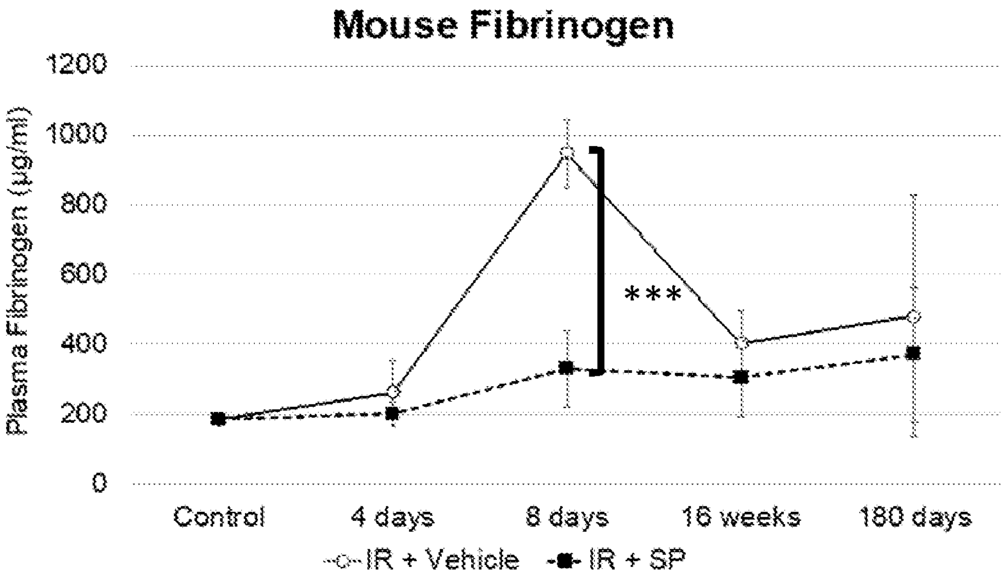
Figure 13C:
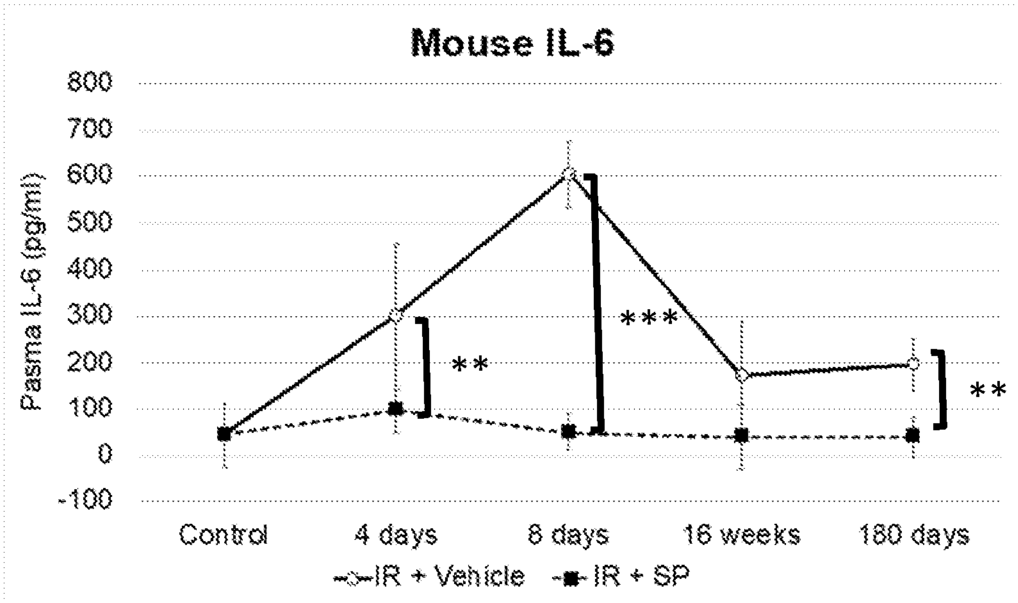
Figure 13D:
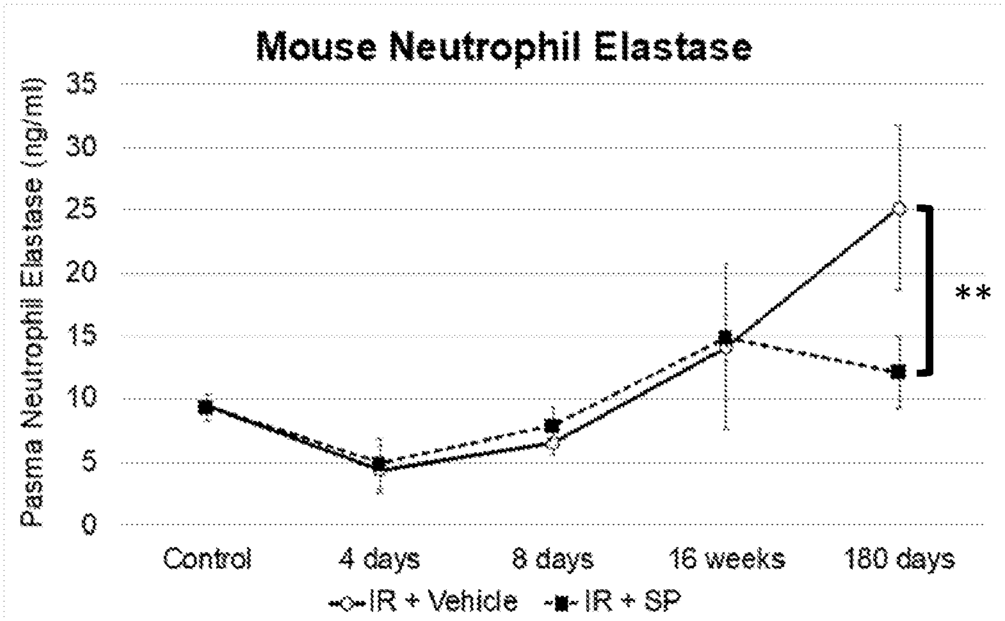
Figure 14A:
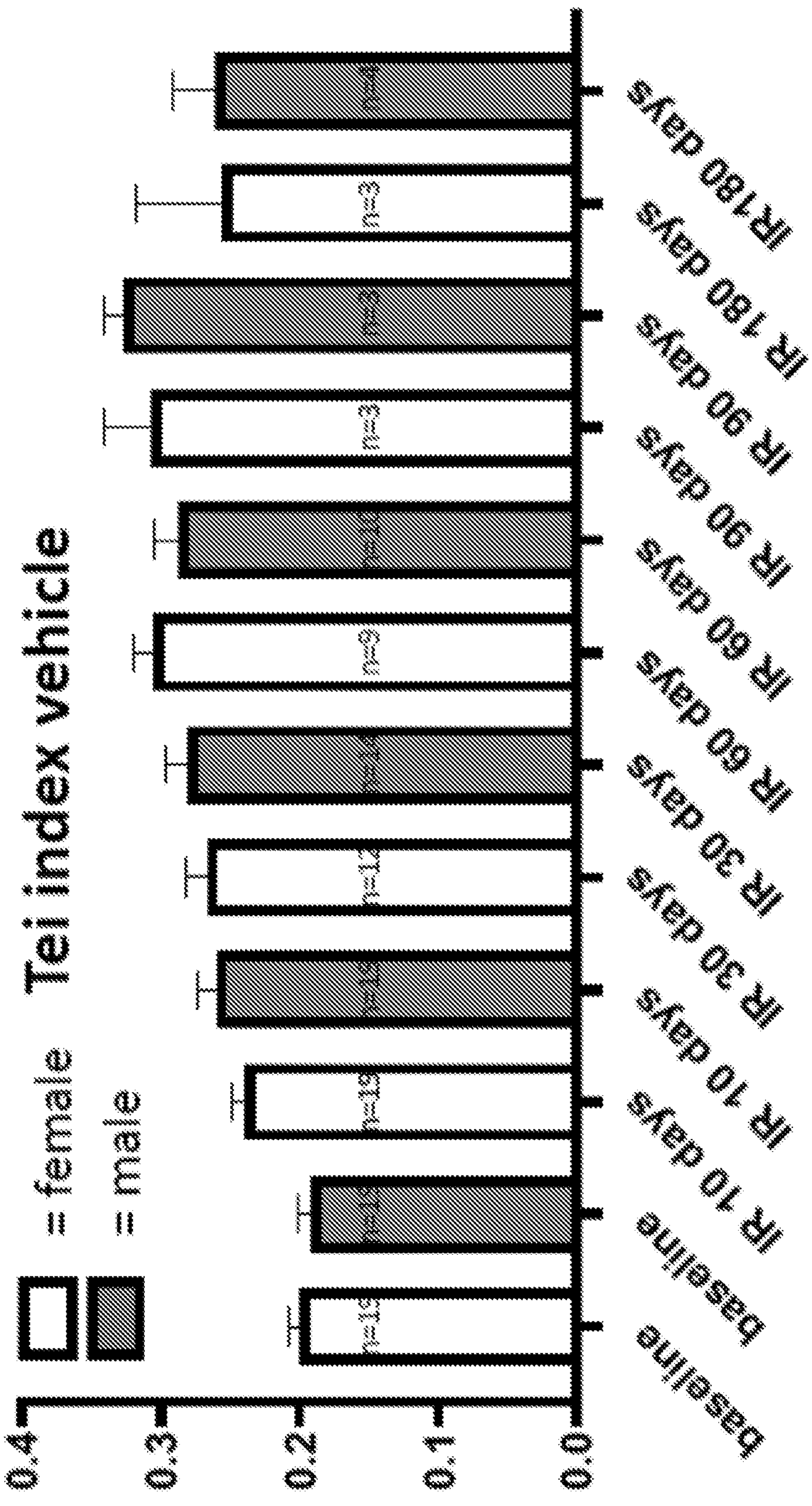
FIGS. 14A-14B illustrate the effect of vehicle (14A) and SP (14B) on systolic function after radiation evaluated by sex.
Figure 14B:
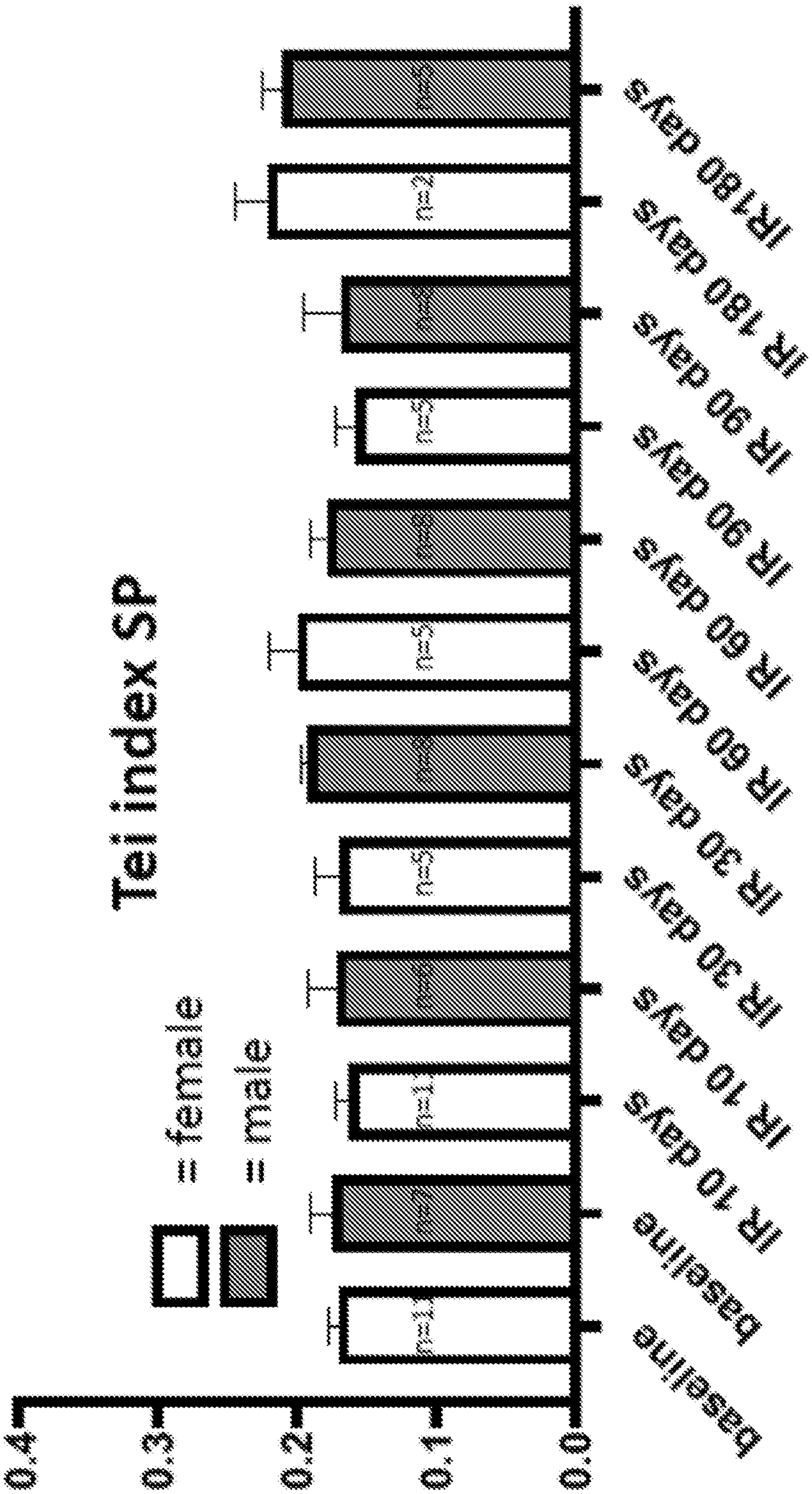
Figure 15A:
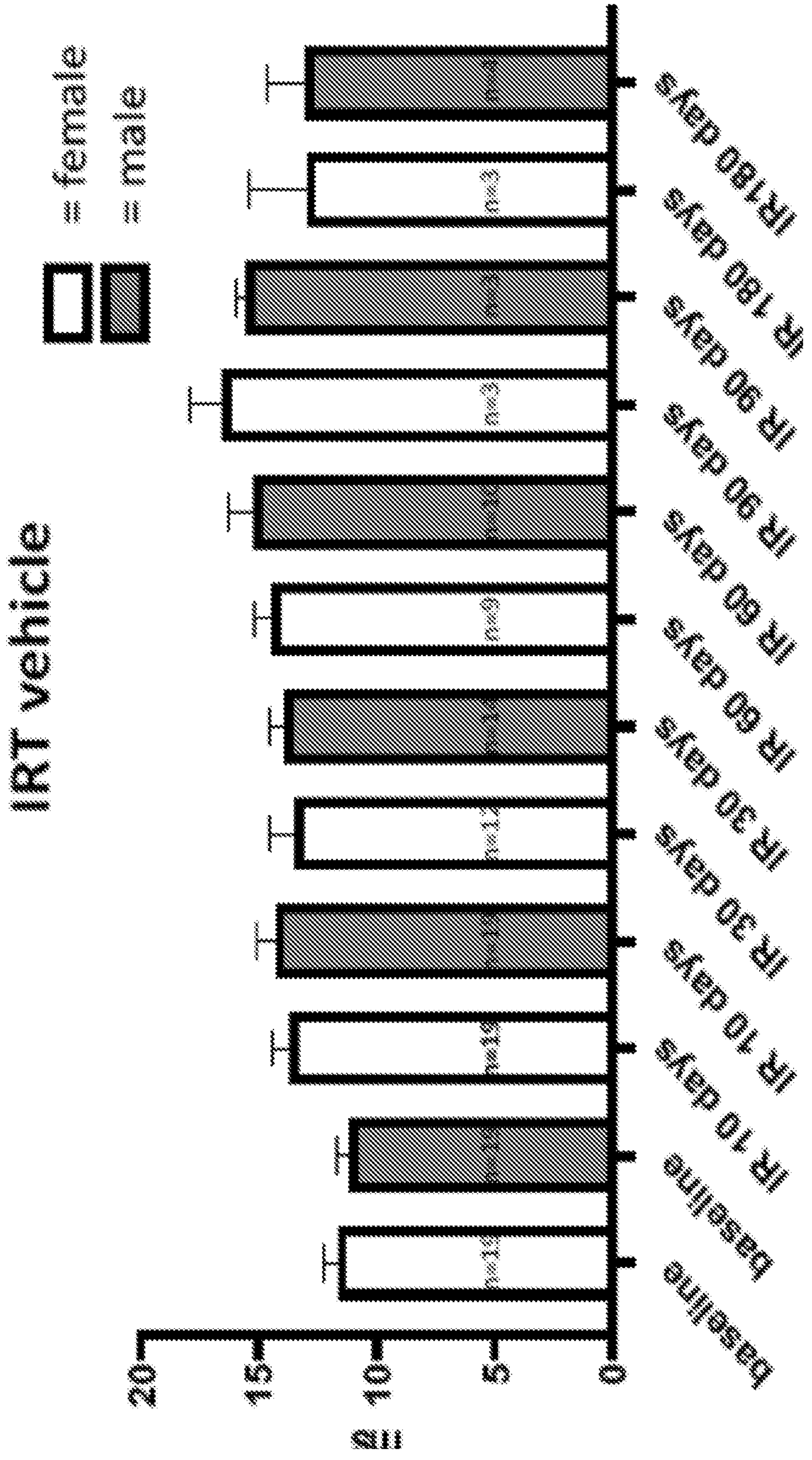
FIGS. 15A-15B illustrate the effect of vehicle (15A) and SP (15B) on diastolic function after radiation evaluated by sex.
Figure 15B:
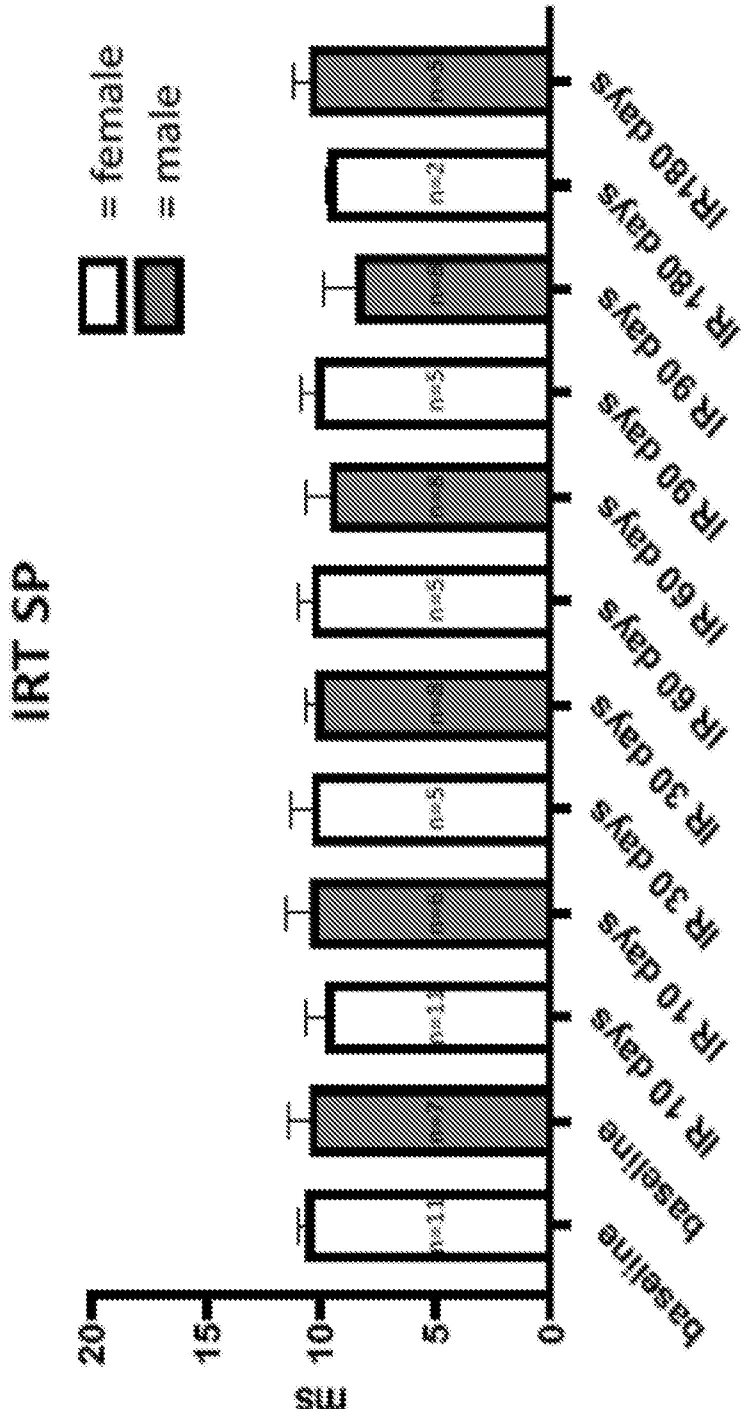

Vehicle-treated group of animals demonstrated significantly higher plasma levels of IL-6 compared with SP-treated group on 4 days, 8 days, and 180 days time-points after IR (304.05±153.23 pg/ml vs 97.00±45.71 pg/ml ($p=0.02$); 606.09±72.72 pg/ml vs 49.85±39.36 pg/ml ($p<0.001$); and 197.22±55.55 pg/ml vs 40.06±43.26 pg/ml (p=0.0/8) respectively) (FIG. 13C). Vehicle-treated group of animals demonstrated significantly higher plasma levels of fibrinogen compared with SP-treated group on 8 days time-point after IR (948.77±98.54 μg/ml vs 332.38±109.02 μg/ml ($p<0.001$)) (FIG. 13B). Vehicle-treated group of animals demonstrated significantly higher plasma levels of neutrophil elastase compared with SP-treated group on 180 days time-point after IR (25.21±6.54 ng/ml vs 12.15±2.87 ng/ml ($p=0.034$)) (FIG. 13 D). C reactive protein did not demonstrate significant difference between vehicle-treated and SP-treated animal groups in any time-points after IR (FIG. 13A).

Figure 12:
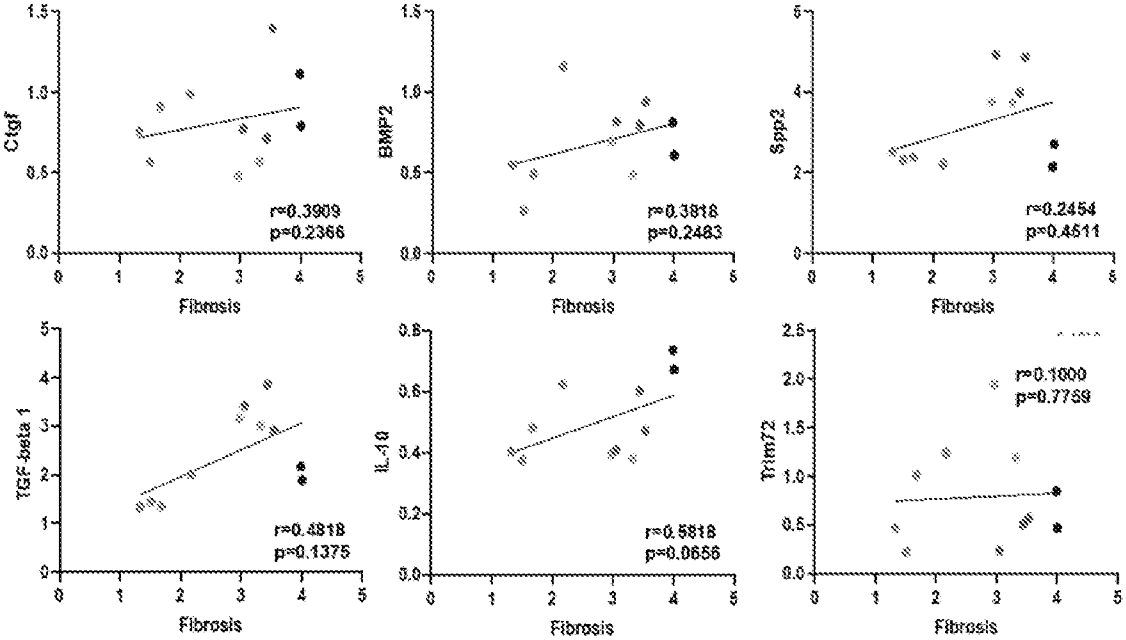
FIG. 12 illustrates the Spearman's correlation between fibrosis and cytokine mRNA relative expression in the lung of vehicle- or SP-treated mice 16 weeks after radiation. Distribution plot of significant Spearman's correlation between fibrosis and cytokine mRNA relative expression in the lungs of vehicle- or SP-treated mice at 16 weeks after radiation. Darkest shades represent mice with higher inflammation/fibrosis. IL=Interleukin, Ccl2=C-C motif chemokine ligand 2, Runx2=Runt-related transcription factor 2 Ccl2=C-C motif chemokine ligand 2, Runx2=Runt-related transcription factor 2, Ctgf=Connective tissue growth factor, Spp2=Secreted Phosphoprotein 2, TGF-beta 1=Tissue Growth Factor-beta 1, BMP2=Bone Morphogenetic Protein 2, Trim72=Tripartite Motif Containing 72, IR=radiation, M=male, F=female, r=Spearman's rank correlation coefficient.

Example 9. Spearman's Correlation Between Fibrosis and Cytokine mRNA Expression Statistical Analysis The two-tailed Student's T-test was used to examine statistical significance in groups with a single independent variable. $P<0.05$ was considered significant. Spearman's rank correlation was used to assess the relationship between specific mRNA expression and degree of lung fibrosis (FIG. 12). Log-rank analysis was used to compare survival among the groups.

Conclusion. Oral administration of BH4 or its metabolic precursor, SP, starting 24 hours after a radiation exposure enhances lung and cardiac function as evidenced by decreasing breathing frequency, enhanced contractile reserve, improved systolic and diastolic function and increased survival.

The invention claimed is:

1. A method of treating a subject exposed to radiation comprising administering an effective amount of sepiapterin, or a pharmaceutically acceptable salt or co-crystal thereof, to the subject, wherein the administering occurs at least once daily for at least six days, wherein:

(a) the subject is exposed to at least 0.3 Gy in less than one day; or (b) the subject is exposed to at least 0.7 Gy over a period of more than one day.

2. The method of claim 1, wherein the effective amount is from about 0.1 to about 200 mg/kg/day.

3. The method of claim 1, wherein the subject has chronic radiation syndrome.

4. The method of claim 1, wherein the administering occurs at least daily for at least 14 days.

5. A method of treating a subject exposed to radiation comprising administering an effective amount of sepiapterin, or a pharmaceutically acceptable salt or co-crystal thereof, to the subject, wherein the administering occurs at least once daily for at least six days, wherein the subject has acute radiation syndrome, and wherein:

(a) the administering occurs within 24 hours after exposure to radiation; or (b) the administering occurs at least 24 hours after exposure to radiation.

6. The method of claim 5, wherein the administering occurs within 24 hours after exposure to radiation.

7. The method of claim 5, wherein the administering occurs at least 24 hours after exposure to radiation.

8. A method of treating a subject exposed to radiation comprising administering an effective amount of sepiapterin, or a pharmaceutically acceptable salt or co-crystal thereof, to the subject, wherein the administering occurs at least once daily for at least six days, wherein the subject has cutaneous radiation syndrome.

* * * * *